US008580533B2

(12) United States Patent
Bouvier et al.

(10) Patent No.: US 8,580,533 B2
(45) Date of Patent: *Nov. 12, 2013

(54) DESTRUCTIBLE SURFACTANTS AND USES THEREOF

(75) Inventors: Edouard S. P. Bouvier, Stow, MA (US); Bruce J. Compton, Lexington, MA (US); John C. Gebler, Hopkinton, MA (US); Martin Gilar, Franklin, MA (US); Ying-Qing Yu, Milford, MA (US); Peter Jeng-Jong Lee, Westborough, MA (US); Elizabeth K. Brown, Sutton, MA (US)

(73) Assignee: Waters Technologies Corporation, Milford, MA (US)

(*) Notice: Subject to any disclaimer, the term of this patent is extended or adjusted under 35 U.S.C. 154(b) by 687 days.

This patent is subject to a terminal disclaimer.

(21) Appl. No.: 10/516,418

(22) PCT Filed: May 30, 2003

(86) PCT No.: PCT/US03/16820
§ 371 (c)(1),
(2), (4) Date: May 13, 2005

(87) PCT Pub. No.: WO03/102225
PCT Pub. Date: Dec. 11, 2003

(65) Prior Publication Data
US 2006/0057659 A1    Mar. 16, 2006

Related U.S. Application Data

(60) Provisional application No. 60/385,021, filed on May 31, 2002.

(51) Int. Cl.
*C12Q 1/37* (2006.01)
*A61K 31/095* (2006.01)

(52) U.S. Cl.
USPC .............................. 435/23; 204/450; 514/706

(58) Field of Classification Search
USPC ................... 435/23; 204/450; 514/236.2, 706
See application file for complete search history.

(56) References Cited

U.S. PATENT DOCUMENTS

| | | | |
|---|---|---|---|
| 2,093,958 A * | 9/1937 | Edquist ........................... | 423/29 |
| 3,948,953 A | 4/1976 | McCoy | |
| 4,925,567 A | 5/1990 | McAleese | |
| 5,523,566 A | 6/1996 | Fuerstenau et al. | |
| 5,607,910 A | 3/1997 | Sherry et al. | |
| 5,817,930 A | 10/1998 | Cojean et al. | |
| 5,961,801 A | 10/1999 | Shieh et al. | |
| 6,096,692 A | 8/2000 | Hagihara et al. | |
| 7,074,936 B2 | 7/2006 | Caprioli et al. | |
| 7,229,539 B1 | 6/2007 | Lee et al. | |

FOREIGN PATENT DOCUMENTS

| | | |
|---|---|---|
| EP | 0242148 | 1/1993 |
| GB | 2 221 989 A | 2/1990 |
| JP | 03281602 A | 12/1991 |
| PL | 162441 | 1/1990 |
| PL | 175563 | 12/1994 |
| PL | 177120 | 6/1995 |
| WO | WO 00/70334 A | 11/2000 |
| WO | WO 02/097393 A2 | 12/2002 |
| WO | WO 02/097393 A3 | 12/2002 |
| WO | WO 03/102536 | 12/2003 |

OTHER PUBLICATIONS

Grabski et al. inNovations Nov. 2001, 13, pp. 10-12.*
Sigma-Aldrich Endoproteinase Glu-C from *Staphylococcus aureus* V8 [online] retrieved from the Internet from http://www.sigmaaldrich.com/catalog/search/ProductDetail?ProdNo=P6181 &Brand=SIGMA on Apr. 25, 2007. 2 pages.*
Taramelli et al. Experimental Parasitology 1995, 81, 501-511.*
Zeller et al. (Journal of Biomolecular Techniques 2002, 13(1), 1-4).*
Meng et al. (Anal Chem 2002, 74, 2923-2929; published on the Web May 9, 2002).*
Grosse, et al. "High-performance liquid chromatographic assay for mothyl-B-cyclodextrin in plasma and coli lysate," Journal of Chromatography B, vol. 694, pp. 219-226 (1997).
U.S. Appl. No. 10/516,419, filed Nov. 29, 2004, Mallet et al.
U.S. Appl. No. 10/169,002, filed Sep. 18, 2002, Lee et al.
Davidsson, P. et al. "Characterization of Proteins From Human Cerebrospinal Fluid By a Combination of Preparative Two-Dimensional Liquid-Phase Electrophoresis And Matrix—Assisted Laser Desorption/Ionization Time-of-Flight Mass Spectrometry", Analytical Chemistry, vol. 71, No. 3, pp. 642-647 (1999).
Hatt, P.D. et al. "Concentration of, and SDS Removal From Proteins Isolated From Multiple Two-Dimensional Electrophoresis Gels", Eur. J. Biochem, vol. 246, pp. 336-343 (1997).
Kawasaki, H. et al. "Separation of Peptides Dissolved in A Sodium Dodecyl Sulfate Solution By Reversed-Phase Liquid Chromatography: Removal of Sodium Dodecyl Sulfate From Peptides Using an Ion-Exchange Precolumn", Analytical Biochemistry, vol. 186, pp. 264-268 (1990).
Laemmli, U.K, "Cleavage of Sgtructural Proteins During The Assembly of the Head of Bacteriophage T4", Nature, vol. 227, pp. 680-685 (1970).
Park, Zee-Yong and Russell, David. H. "Identification of Individual Proteins In Complex Protein Mixtures By High-Resolution, High-Mass-Accuracy MALDI TOF-Mass Spectrometry Analysis of In-Solution Termal Denaturation/Enzymatic Digestion", Anal. Chem., vol. 73, No. 11, pp. 2558-2568 (2001).
Piasecki, Andrzej and Mayhew, Alexandra, "Synthesis And Surface Properties of Chemodegradable Anionic Surfactants: Diastereomeric (2-n-alkyl-1,3-dioxan-5-yl) Sulfates With Monovalent Counter-Ions", Journal of Surfactants and Detergents, vol. 3, No. 1, pp. 59-65 (2000).

(Continued)

*Primary Examiner* — Blessing Fubara
*Assistant Examiner* — Kauser M Akhoon
(74) *Attorney, Agent, or Firm* — Edwards Wildman Palmer LLP; Nicholas J. DiCeglie, Jr.

(57) ABSTRACT

The present invention provides methods for enhancing chemical reactions of molecules, e.g., biomolecules, with destructible surfactants. The chemical reactions may involve and/or be associate with analysis, e.g., solubilizing, separating, purifying and/or characterizing the molecules. In one aspect, the anionic surfactants of the present invention may be selectively broken up at relatively low pH. The resulting breakdown products of the surfactants may be removed from the molecule/sample with relative ease. The invention has applicability in a variety of analytical techniques.

26 Claims, 13 Drawing Sheets

(56) References Cited

OTHER PUBLICATIONS

Piasecki, et al. Bulletin of the Polish Academy of Sciences-Chemistry, vol. 45, pp. 329-337 (1997).

Piasecki, et al. "Synthesis, Surface Properties, and Hydrolysis of Chemodegradable Anionic Surfactants: DiastereomericallY Pure cis- and trans-2,5-Disubstituted-1,3-dioxanes", J. Colloid and Interface Science, vol. 192, pp. 74-82 (1997).

Ross, Andrew R.S. et al. "Identification of Proteins From Two-Dimensional Polyacrylamide Gels Using A Novel Acid-Labile Surfactant", Proteomics, vol. 2, pp. 928-936, (2002).

Russell, William K. et al. "Proteolysis In Mixed Organic-Aqueous Solvent System: Appilcations For Peptide Mass Mapping Using Mass Spectrometry", Anal. Chem., vol. 73, No. 11, pp. 2682-2685 (2001).

Schively, J.E. "Methods of Protein Microcharacterization", Schively, Ed. Jumana Press, Clifton, NJ, pp. 41 (1996).

Yamamura, "Studies on Synthesis of Surfactants With Specific Functions", Yukagaku, vol. 43, pp. 2-9 (1994).

Jaeger, D.A., et al., "Preparation and characterization of glycerol-based cleavable surfactants and derived vesicles" Journal of the American Chemical Society, vol. 111, No. 8, 1989, pp. 3001-3006, XP002447685 ISSN: 0002-7863.

Staudenmann, W., et al., "Sample handling for proteome analysis" Electrophoresis, vol. 19, No. 6, May 1998, pp. 901-908, XP002447686 ISSN: 0173-0835.

Piasecki, A., et al. "Chemical Structure and Surface Activity. XXXII. (+) Synthesis and Surface Properties of Chemodegradable Surfactants: Sodium cis-[2-n-alkyl-5-methyl-1,3-dioxan-5yl)methyl] Sulfates," Bulletin of the Polish Academy of Sciences Chemistry, vol. 45, No. 3 (1997).

Compton, B. J., et al.; "Proceedings of the 47th ASMS Conference on Mass Spectrometry and Allied Topics, Dallas, TX", (1999).

Compton, B. J., et al.; "A Novel SDS Analog Compatible with MS Analysis of Proteins and Peptides", (Poster #MPI 243) Milford, MA (1999).

Ross, A. R. S., et al.; "Proceedings of the 48th ASMS Conference on Mass Spectrometry and Allied Topics", Long Beach, CA, (2000).

Ross, Andrew, R.S., et al. Evaluation of a SDS Analogue for 2-D Page and MALDI/Tof MS Mapping of Proteins Using Automated Spot Cutting and In-gel Digestion Procedures (Poster) (2000).

Zeller, M., et al.; Proceedings of the 49th ASMS Conference on Mass Spectrometry and Allied Topics, Chicago, IL, (2001).

Zeller, M., et al. "Use of an Acid-Labile Surfactant as SDS Substitute for Gel Electrophoresis and Digest Analysis", (Abstract and Poster) Milford, MA (2001).

\* cited by examiner

Trypsin Activity

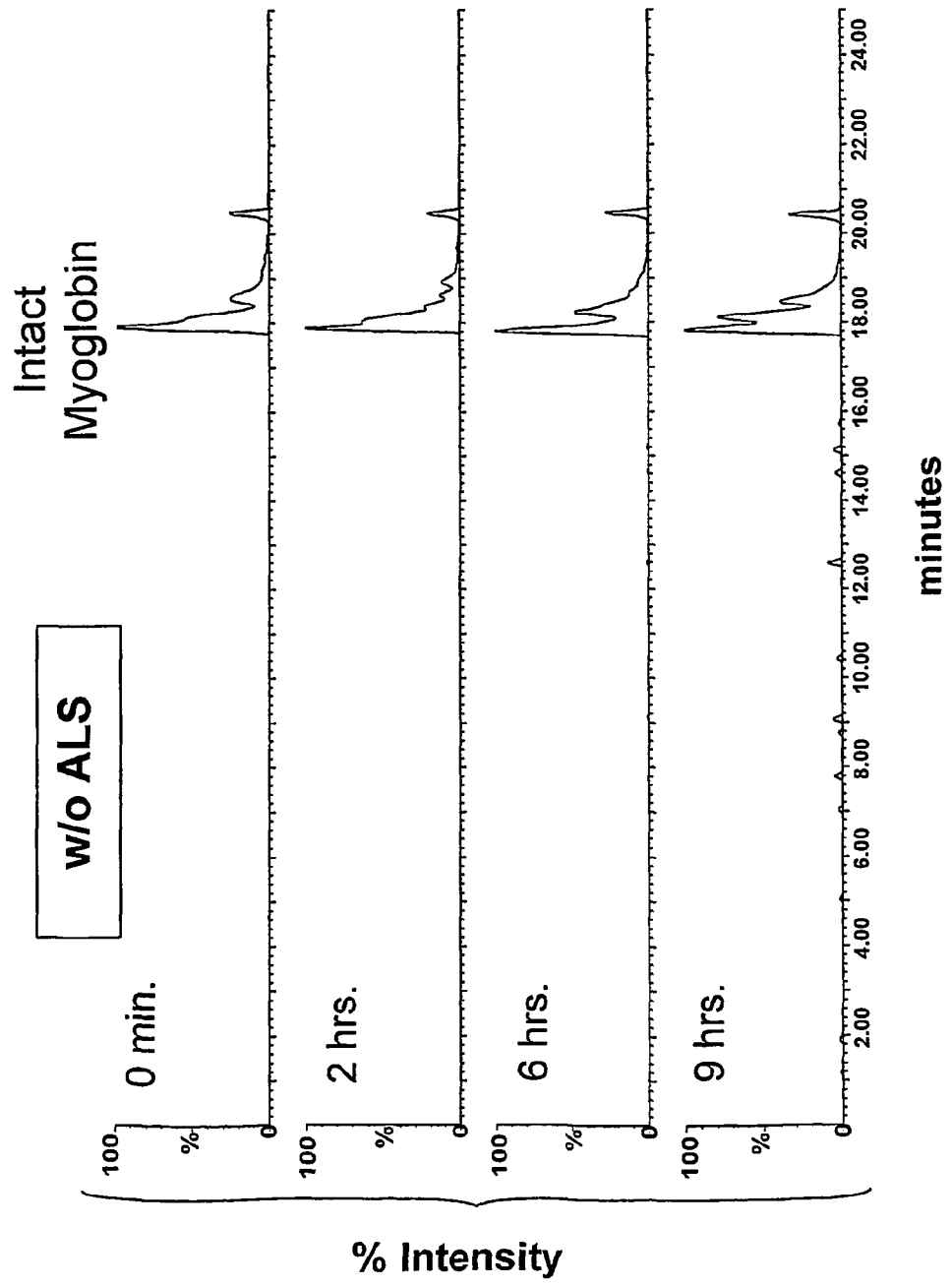

MALDI-TOF Analysis of Trypsin Digestion of Myoglobin

DESTRUCTIBLE SURFACTANTS AND USES THEREOF

REFERENCE TO RELATED APPLICATIONS

This application is a U.S. national phase application, pursuant to 35 U.S.C. §371, of PCT international application Ser. No. PCT/US03/16820, filed 30 May 2003 designating the United States, and published in English as international publication WO 03/102225 A1 on 11 Dec. 2003, which claims priority to U.S. provisional application Ser. No. 60/385,021, filed on May 31, 2002. This application is related to U.S. Patent Application No. 60/134,113, filed on May 14, 1999, and published PCT International application No. WO 00/70334, published Nov. 23, 2000; (application No. PCT/US00/13028, filed on May 12, 2000). The entire contents of the aforementioned patent applications are incorporated herein by this reference.

BACKGROUND OF THE INVENTION

Surfactants are used in a variety of applications. For example, surfactants are used commercially for cleaning manufactured items, removing paints, chemical processing, for use in emulsion polymerization, solubilizing drugs, purifying proteins, and various bioanalytical applications.

In addition, surfactants have been employed in chemical alteration reactions, e.g., reduction or alkylation, involving biomolecules, such as proteins, for solubilization, or the surfactants are present in the reaction as an artifact of the process of preparation, e.g., electrophoresis. Reactions, e.g., reduction and alkylation, of large proteins are important steps for in-solution digestion because of their ability to increase the number of peptide fragments. Organic salts, such as urea and detergents, e.g., sodium dodecylsulfate (SDS), are commonly used to solubilize protein mixtures before reduction and alkylation. However, urea and SDS inhibit trypsin activity, and therefore their concentrations have to be diluted prior to in-solution trypsin digestions. Additionally, it is known that if digestion, in which urea has been utilized as a solubilizing agent, is allowed to proceed for too long, the urea will act upon and modify the protein, making analysis of peptide fragments more difficult and inaccurate.

Furthermore, SDS and urea are also known to suppress the MS signal if they are not removed. The additional sample preparation steps that are required for current methodologies decrease the reliability and sensitivity of the analysis, especially for low abundance proteins.

Another particular bioanalytical application that uses surfactants is sodium dodecyl sulfate polyacrylamide gel electrophoresis (SDS-PAGE). In the past three decades, SDS-PAGE has been widely used as a simple and relatively rapid tool for analysis and purification of large molecules such as proteins (U. K. Laemmli, Nature 227, 680-685, 1970). Sodium dodecylsulfate (SDS) is an anionic surfactant that denatures proteins by forming a stable complex. Upon denaturation, SDS binds to most proteins and peptides in a constant weight ratio of about 1.4:1. As a result, the SDS-protein complexes have almost identical charge densities and therefore migrate in a polyacrylamide gel according to molecular weight. If the gel is of the correct porosity, a plot of log $M_w$ vs. relative mobility, $R_f$, results in a linear relationship. The band intensity after staining is a rough indicator of the amount present in the sample. When coupled with another electrophoretic technique, isoelectricfocusing, SDS-PAGE can separate complex mixtures into several hundred discrete components.

The ability to estimate the size and amount of a protein has led to various applications of SDS-PAGE. However, there are some drawbacks to the technology. For example, it is very difficult to use mass spectrometry to monitor and analyze samples from SDS-PAGE separations because SDS interferes with the sensitivity of mass spectrometry detection. Furthermore, it is very difficult to separate SDS from SDS/protein complex since SDS is a surfactant that forms emulsions.

Protein digestion to produce protein fragments is an important aspect of protein characterization. Currently, the rate-limiting step in mass spectrometric analysis of protein fragments is the extended time required for digestion, e.g., typically 12 hours or more as in the case of trypsin digestion of proteins. Furthermore, the large amounts of trypsin required in current protocols can result in increased background noise due to trypsin autolysis. In addition, the current approaches to trypsin digestion result in mass spectrometric identification of only a limited number of the peptide fragments, e.g., about 60%.

It is also known in the art that trypsin digestion can be accelerated by: (1) performing the digestion at elevated temperatures (Anal. Chem. 2001, 73, 2558-2564); (2) in the presence of certain organic solvents (Anal. Chem. 2001, 73, 2682-2685); or (3) using immobilized trypsin. However, these methods often result in miscleavages, or are difficult to reproduce. Therefore, when it is desirable to generate a reproducible peptide map, the preferred methodology is overnight incubation, often done at low temperature. Nevertheless, a method for enhancing (e.g., acceleration with high reproducibility and low miscleavage) the digestion of proteins is desired.

SUMMARY OF THE INVENTION

The present invention provides methods for enhancing chemical reactions of molecules, e.g., biomolecules, with destructible surfactants. The chemical reactions may involve and/or be associated with analysis, e.g., solubilizing, separating, purifying, detecting and/or characterizing the molecules. For example, in one embodiment, a compound of the invention, e.g., sodium 4-[(2-methyl-2 undecyl-1,3-dioxolan-4-yl) methyl]-1-propanesulfonate (ALS), may be useful as an additive, e.g., denaturant, for separation of intact proteins and peptides in various techniques of HPLC (i.e., such that the separation using HPLC may be considered the chemical reaction). In one aspect, the anionic surfactants of the present invention may be selectively broken up at relatively low pH. The resulting breakdown products of the surfactants may be removed from the sample with relative ease.

The invention has applicability in a variety of techniques that benefit from the initial presence and ultimate removal of a surfactant. Moreover, the surfactants of the invention allow for more rapid, reproducible, relatively low temperature, e.g., room temperature, protease, e.g., trypsin, digestion of a biomolecule, e.g., protein, which requires less protease due to enhanced efficiency of the reaction without concomitant increase in miscleavages. In fact, the digestions of the present invention are more complete than those of current methodology and therefore afford an increased number of correctly cleaved peptide fragments.

The elimination of excess trypsin, surfactants, and organic solvents from the protease digestions eliminates mass spectrometric suppression and reduces background noise which would otherwise be due to trypsin autolysis, therefore improving analysis of low abundance biomolecules. The reduction of time required for digestion further lends itself to rapid on-line, automated digestion and analysis.

In addition, the elimination of sample preparation steps required with current methodology increases the reliability and sensitivity of the analysis, especially for low abundance proteins. In certain embodiments, the surfactants of the present invention will not act upon and will not modify the protein, reducing the difficulty of analysis of peptide fragments, as compared, e.g., with the use of urea as a surfactant.

Accordingly, one embodiment of the invention provides a method for enhancing a chemical reaction of a molecule comprising contacting the molecule with a surfactant represented by formula I:

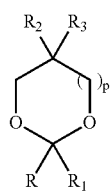

in which
p is 0, 1 or 2;
R is alkyl;
$R_1$ and $R_2$ are each, independently, hydrogen or methyl; and
$R_3$ is selected from $-OSO_3^-$, $-R_4OSO_3^-$, $-R_4OR_5SO_3^-$, and $-OR_5SO_3^-$,
wherein $R_4$ and $R_5$ are each, independently, lower alkyl;
to thereby enhance the chemical reaction of the molecule.

In another aspect, the invention pertains a method for analysis of a biomolecule comprising: enhancing a chemical reaction of the biomolecule by contacting a sample containing the biomolecule with a surfactant represented by Formula I, and analyzing the sample to thereby analyze the biomolecule.

Another aspect of the invention provides a kit for enhancing a chemical reaction of a molecule comprising a surfactant represented by formula I, and instructions for use.

In yet another aspect, the invention provides a method of capturing a lipophilic compound comprising contacting a lipophilic compound with a surfactant represented by formula (I), and degrading the surfactant to produce a hydrophobic compound, to thereby capture the lipophilic compound.

In an additional aspect, the invention provides a method for enhancing surface desorption ionization analysis of a molecule comprising: contacting the molecule with a surfactant represented by formula (I), to thereby analyze the sample by surface desorption ionization.

In yet another aspect, the invention provides a method for enhancing chemical digestion of a biomolecule comprising: contacting the molecule with a digestive enzyme and a surfactant represented by formula I, to thereby enhance the chemical digestion of the molecule.

Another aspect of the invention provides a kit for enhancing chemical digestion of a biomolecule comprising a surfactant represented by formula I, and instructions for use.

BRIEF DESCRIPTION OF THE DRAWINGS

FIGS. 2A-2B show the LC/MS TIC of tryptic digested myoglobin solubilized with (A) 0.1% ALS or (B) 50 mM $NH_4HCO_3$ (no ALS).

FIG. 6A is the spectrum of 5 μM myoglobin in 50/50 20 mM ammonium acetate/water with 1% acetic acid. FIG. 6B is the spectrum of 5 μM myoglobin in 50/50 20 mM ammonium acetate/water with 1% acetic acid and 0.1% SDS. FIG. 6C is the spectrum of 5 μM myoglobin in 50/50 20 mM ammonium acetate/water with 1% acetic acid and 0.1% ALS that had reacted in 10% acetic acid for 16 hours.

DETAILED DESCRIPTION OF THE INVENTION

Overview of the Invention

Figure 1:
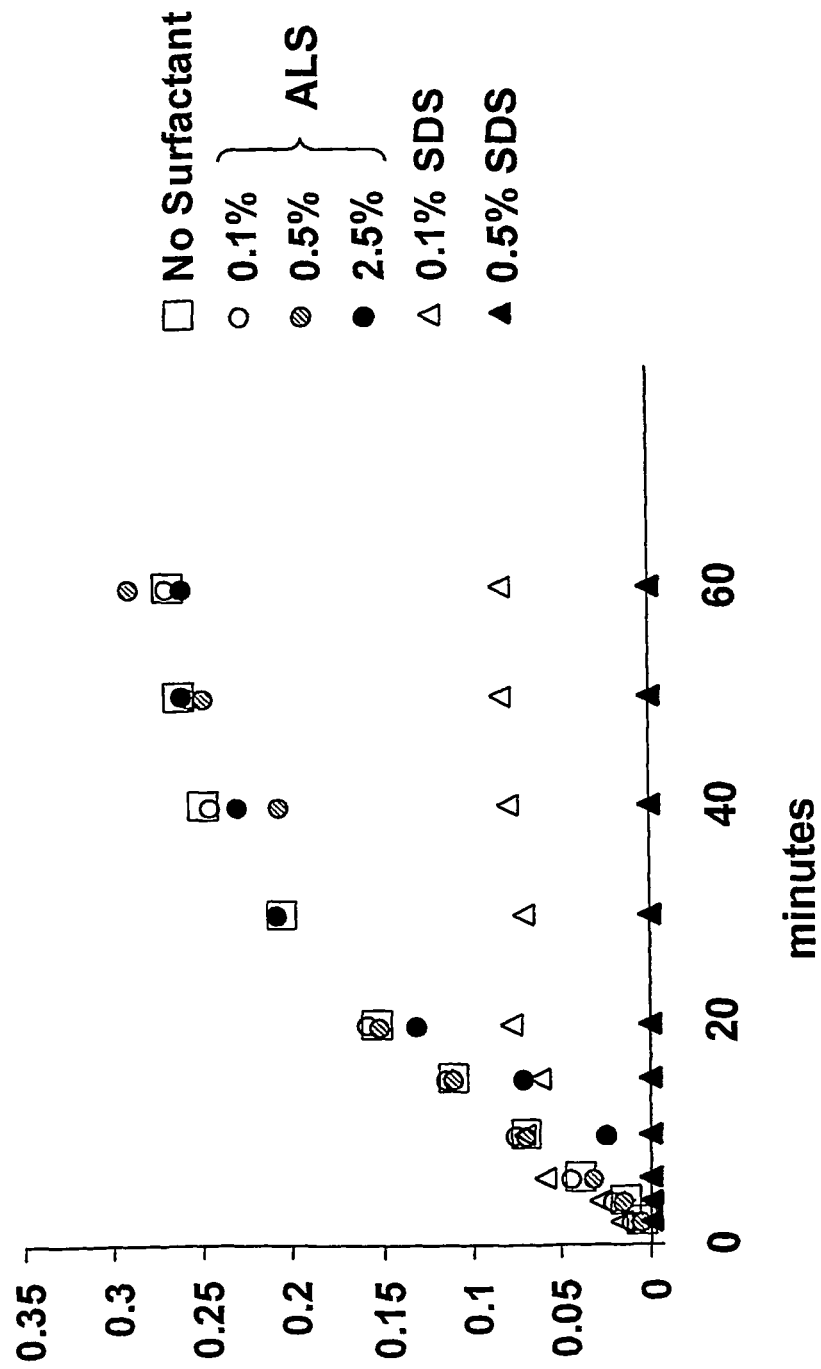
FIG. 1 shows the analysis to determine the trypsin activity, indicating that SDS inhibits trypsin activity at each the percentages examined.

The invention provides methods for enhancing chemical reactions of molecules, e.g., biomolecules, with destructible surfactants. The chemical reactions may involve and/or be associated with analysis, e.g., solubilizing, separating, purifying, detecting and/or characterizing the molecules. For example, in one embodiment, a compound of the invention, e.g., ALS, may be useful as an additive, e.g., denaturant, for separation of intact proteins and peptides in various techniques of HPLC (i.e., such that the separation using HPLC may be considered the chemical reaction). In particular, the invention includes anionic surfactants with binding and electrophoretic properties similar to SDS. However, the surfactants of the present invention, unlike SDS, include a dioxolane or dioxane functional group that enable degradation of the surfactant under an acidic environment. The resulting degradant products can be removed from the sample more readily than the original surfactant. In addition, mass spectrometric sensitivity of the molecules is significantly and surprisingly greater in the presence of the surfactants of the invention than in the presence of SDS at similar concentrations, even in the presence of these degradant products. The invention has applicability in a variety of techniques that benefit from the initial presence and ultimate removal of a surfactant.

Moreover, the surfactants of the invention allow for more rapid, reproducible, relatively low temperature, e.g., room temperature, protease, e.g. trypsin, digestion of a biomolecule, e.g., protein, which requires less protease due to enhanced efficiency of the reaction without concomitant increase in miscleavages. In fact, the digestions of the present invention are more complete than those of current methodology and therefore afford an increased number of correctly cleaved peptide fragments.

The elimination of excess trypsin, surfactants, and organic solvents from the protease digestions eliminates mass spectrometric suppression and reduces background noise which would otherwise be due to trypsin autolysis, therefore improving analysis of low abundance biomolecules. The reduction of time required for digestion further lends itself to rapid on-line, automated digestion and analysis.

In addition, the elimination of sample preparation steps required with current methodology increases the reliability and sensitivity of the analysis, especially for low abundance proteins. In certain embodiments, the surfactants of the present invention will not act upon and will not modify the protein, reducing the difficulty of analysis of peptide fragments, as compared with the use, e.g., of urea as a surfactant.

DEFINITIONS

So that the invention may be more readily understood, the definitions of a several terms used throughout the specification and claims are presented here.

The language "sample/surfactant complex" is intended to include a complex formed by a surfactant of the present invention and a component of the sample.

The term "molecule" as used herein is intended to include any chemical entity that may be used within the methods of the present invention. This term is intended to include small molecules and macromolecules, either of which may be classified as a biomolecule.

The term "biomolecule" includes chemical entities that are obtained from biological sources. Exemplary biomolecules include, but are not limited to, substances, such as biopolymers, e.g., proteins, e.g., proteolytic proteins or lipophilic proteins, such as receptors and other membrane-bound proteins, and peptides.

The language "biological sample" refers to any solution or extract containing a molecule or mixture of molecules that comprises at least one biomolecule that is subjected to analysis that originated from a biological source. Biological samples are intended to include crude or purified, e.g., isolated or commercially obtained, samples. Particular examples include, but are not limited to, inclusion bodies, biological fluids, biological tissues, biological matrices, embedded tissue samples, and cell culture supernatants.

The language "biological fluid" is intended to include biologically produced fluids such as blood, blood plasma, urine, spinal fluid, mucosal tissue secretions, tears, interstitial fluid, synovial fluid, semen, and breast milk.

The term "lipophilic protein" refers to proteins or peptides that are relatively hydrophobic. Particular examples include, without limitation, protein from myelin or central nervous system tissue and membrane-bound proteins such as receptors.

The term "receptor" is recognized in the art and refers generally to membrane-bound molecules, preferably proteins, which bind a ligand and transmit a signal into the cell. Such receptors usually have an extracellular domain, a transmembrane domain, and an intracellular domain.

The term "inclusion body" is recognized in the art and refers to an intracellular structure, preferably one containing an expressed protein.

The language "enhancing surface desorption ionization" is intended to include the act of improving the quality of analytical results obtained from surface desorption ionization techniques. The improvement includes, without limitation, enhancement through increased solubility of an analyte of interest or improved desorption ionization as a result of denaturation.

The language "enhancing a chemical reaction" is intended to include the act of influencing a chemical reaction to produce a favorable chemical property.

The language "favorable chemical property" is intended to include properties of a chemical reaction of the invention that are advantageous over known methodology. Examples of a favorable chemical property include, but are not limited to, more complete reaction, e.g., better cleavage of peptidic fragments resulting from chemical digestion, increased efficiency, i.e., less protease per total protein ratio required for digestion, increased yield, increased rate, e.g., accelerating chemical digestion, e.g., from hours to minutes, e.g., about 20 hours to about 5 minutes for trypsin digestion, and increased utility. Examples of favorable chemical properties that relate to chemical reactions that involve analysis may include, without limitation, improved separation, improved purification, increased solubilization, increased detection, and improved characterization of molecules.

The language "increased utility" is intended to include the use of a chemical reaction process on compounds not typically used, or previously demonstrated by alternative methods to be unreactive. For example, the use of the surfactants of the present invention affords the ability to facilitate digestion, e.g., tryptic digestion, of proteins that are difficult or impossible to digest by other methods, or facilitate correct digestion of proteins that may have occurred by other known methods, although with numerous miscleavages.

The terms "denature", "denaturing" or "denaturation" are used interchangeably and intended to include the modification of the molecular structure of a biomolecule, such as a protein or DNA, by the surfactants of the invention, heat, acid, alkali, or ultraviolet radiation, so as to destroy or diminish some of the original properties, e.g., three-dimensional conformation, and especially the specific biological activity.

The language "chemical reaction" is intended to include a chemical transformation or change as the result of an interaction of chemical entities. In particular embodiments of the invention, the chemical reaction is chemical digestion or chemical alteration. The chemical reactions may involve and/or be associated with analysis, e.g., solubilizing, separating, purifying, detecting and/or characterizing the molecules. For example, in one embodiment, a compound of the invention, e.g., sodium 4-[(2-methyl-2 undecyl-1,3-dioxolan-4-yl)methyl]-1-propanesulfonate (ALS), may be useful as an additive, e.g., denaturant, for separation of intact proteins and peptides in various techniques of HPLC (i.e., such that the separation using HPLC may be considered the chemical reaction).

The language "chemical digestion" is intended to include a process of breaking down a molecule, e.g., a biomolecule, e.g., a protein, into simpler chemical compounds, e.g., fragments. In one embodiment, the chemical digestion is performed by an enzyme, e.g., a protease, reaction with CNBr, or reaction with hydroxylamine. Proteases of the present invention include both specific, e.g., trypsin, and nonspecific, e.g. pepsin, or papain, proteases. In certain embodiments, the chemical digestion results in breaking of amide bonds. In specific embodiments of the invention, the chemical digestion results in breaking designated amide bonds.

The language "chemical alteration" is intended to include any chemical reaction of a molecule that is not a chemical digestion. In certain embodiments, the chemical alteration produces a chemically or physically, e.g., solubilization, altered molecule. In certain other embodiments, the chemical alteration does not produce a chemically or physically altered molecule, i.e., catalysis has occurred. In particular embodiments the chemical alteration is alkylation, reduction, e.g., using dithiothreitol (DTT), or a combination thereof.

The language "solution for degrading the surfactant" refers to any relatively low pH solution. Preferably, the pH of the solution is between about 0 and about 5, more preferably between about 1 and about 3. In general, the lower the pH of the solution for degrading the surfactant, the less time required to degrade the surfactant. In addition, the compound used to make the solution for degrading the surfactant is not particularly limited: any compound that provides a relatively low pH solution suitable for degrading the surfactants of the present invention without damaging the sample is sufficient. Thus, for example, hydrochloric acid, acetic acid, formic acid, or trifluoroacetic acid (TFA) may be used as the solution for degrading the surfactant. In particular embodiments, TFA may be used to degrade the surfactant. In other particular embodiments, acetic or formic acid may be used as the solution for degrading the surfactant. In certain embodiments, the removal of one of the two components of the degraded surfactant may be accomplished by removing the oily layer formed after degradation.

The term "electrophoresis" refers to any of the various methods of analyzing molecules by their rate of movement in an electric field, i.e. based on the charge to mass ratio of the molecules. Examples include, but are not limited to, gel electrophoresis, polyacrylamide gel electrophoresis, including the tube, slab gel and capillary formats of polyacrylamide gel electrophoresis, free zone electrophoresis and capillary electrophoresis.

The terms "analysis" or "analyzing" are used interchangeably and refer to any of the various methods of separating, detecting, isolating, purifying, solubilizing, and/or characterizing molecules, such as, e.g., intact proteins, petides, and fragments thereof. Examples include, but are not limited to, solid phase extraction, solid phase micro extraction, electrophoresis, mass spectrometry, e.g., Matrix Assisted Laser Desorption Ionization-Mass Spec (MALDI-MS) or Electrospray Ionization (ESI), liquid chromatography, e.g., high performance, e.g., reverse phase, normal phase, or size exclusion, ion-pair liquid chromatography, liquid-liquid extraction, e.g., accelerated fluid extraction, supercritical fluid extraction, microwave-assisted extraction, membrane extraction, soxhlet extraction, precipitation, clarification, electrochemical detection, staining, elemental analysis, Edmund degradation, nuclear magnetic resonance, infrared analysis, flow injection analysis, capillary electrochromatography, ultraviolet detection, and combinations thereof.

In certain embodiments, the surfactant of the invention is degraded prior to analysis. In alternative embodiments, the surfactant of the invention, e.g. ALS, is not degraded prior to analysis. In particular, a surfactant of the invention, such as ALS does not need to be degraded prior to analysis by HPLC or MS (i.e., analysis may be performed prior to degradation). For example, in one embodiment, on-column degradation (e.g., allowing the surfactant to remain at elevated temperatures on the column for longer periods of time, e.g., 20 minutes at 60° C.) may be used to degrade the surfactant during the analysis. Alternatively, the surfactant of the invention may not require degradation during analysis.

The language "compatible with" is intended to mean that the surfactants of the invention and/or the degradation products thereof, do not interfere with and/or enhance the analysis and/or a chemical reaction of a molecule.

The term "clarification" refers to any process by which insoluble particulate matter is separated from the liquid phase.

The term "mass spectrometric detection" refers to any of the various methods of mass spectroscopy. Examples include, but are not limited to, electrospray ionization ("ESI"), surface desorption ionization techniques, and atmospheric pressure chemical ionization (APCI).

The language "surface desorption ionization" is intended to include mass spectrometry, such as MALDI-MS, desorption ionization on silicon (DIOS), thermal desorption mass spectrometry, or surface enhanced laser desorption ionization (SELDI) where desorption ionization is accomplished on a surface, with or without a matrix assistance.

The language "hydrocarbon" includes substituted or unsubstituted alkyl, alkenyl, alkynyl, or aryl moieties.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_{20}$ for straight chain, $C_3$-$C_{20}$ for branched chain), and more preferably 20 or fewer. Likewise, preferred cycloalkyls have from 3-8 carbon atoms in their ring structure, and more preferably have 5 or 6 carbons in the ring structure.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), allyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_1$-$C_{20}$ for straight chain, $C_3$-$C_{20}$ for branched chain). Likewise, cycloalkenyl groups may have from 3-8 carbon atoms in their ring structure, and more preferably have 5 or 6 carbons in the ring structure.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_1$-$C_{20}$ for straight chain, $C_3$-$C_{20}$ for branched chain).

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to ten carbon atoms. "Lower alkenyl" and "lower alkynyl" have chain lengths of, for example, 2 to 6 carbon atoms, more preferably 3 or 4 carbon atoms.

The term "acyl" includes compounds and moieties that contain the acyl radical ($CH_3CO-$) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alknyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide" or "aminocarboxy" includes compounds or moieties that contain a nitrogen atom which is bound to the carbon of a carbonyl or a thiocarbonyl group. The term includes "alkaminocarboxy" groups which include alkyl, alkenyl, or alkynyl groups bound to an amino group bound to a carboxy group. It includes arylaminocarboxy groups that include aryl or heteroaryl moieties bound to an amino group that is bound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group.

The term "carbonyl" or "carboxy" includes compounds and moieties that contain a carbon connected with a double bond to an oxygen atom. Examples of moieties that contain a carbonyl include aldehydes, ketones, carboxylic acids, amides, esters, anhydrides, etc.

The term "thiocarbonyl" or "thiocarboxy" includes compounds and moieties that contain a carbon connected with a double bond to a sulfur atom.

The term "ester" includes compounds and moieties that contain a carbon or a heteroatom bound to an oxygen atom that is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "ether" includes compounds or moieties that contain an oxygen bonded to two different carbon atoms or heteroatoms. For example, the term includes "alkoxyalkyl" which refers to an alkyl, alkenyl, or alkynyl group covalently bonded to an oxygen atom that is covalently bonded to another alkyl group.

The term "thioether" includes compounds and moieties that contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom that is bonded to an alkyl group. Similarly, the term "alkthioalkenyls" and alkthioalkynyls" refer to compounds or moieties wherein an alkyl, alkenyl, or alkynyl group is bonded to a sulfur atom that is covalently bonded to an alkynyl group.

The term "hydroxy" or "hydroxyl" includes groups with an —OH or —O⁻.

The term "halogen" includes fluorine, bromine, chlorine, iodine, etc. The term "perhalogenated," e.g., perfluorinated, generally refers to a moiety, e.g., perfluorocarbons, wherein all hydrogens are replaced by halogen atoms, e.g., fluorine.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

Compounds of the Invention

The destructible surfactants of the invention may be prepared as shown in Scheme 1 set forth in Example 1 below. These surfactants have functionality similar to sodium dodecylsulfate (SDS) but, unlike SDS, they may be hydrolyzed in aqueous acid solution under mild condition to give two non-surfactant products: an ionic, water-soluble compound and a neutral, water-insoluble, hydrophobic compound.

In one embodiment, the anionic surfactants of the invention have the structure of the general formula (Formula I):

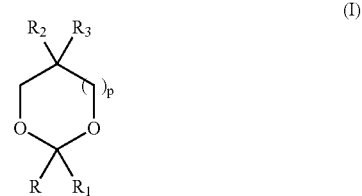

in which p is 0, 1 or 2;

R is alkyl;

$R_1$ and $R_2$ are each, independently, hydrogen or methyl; and $R_3$ is selected from —$OSO_3^-$, —$R_4OSO_3^-$, —$R_4OR_5SO_3^-$; and —$OR_5SO_3^-$;

wherein $R_4$ and $R_5$ are each, independently, lower alkyl.

In certain embodiments, the surfactants have the structure of Formula I, with the provisos that when p is 0 and $R_1$ is methyl, $R_3$ is not —$CH_2O(CH_2)_4SO_3^-$ or, when p is 1 and $R_1$ is hydrogen and $R_2$ is methyl, $R_3$ is not —$CH_2OSO_3$.

In particular embodiments, p is 0 or 1. In other particular embodiments, R is an alkyl having from six to twenty carbon atoms, more specifically from eight to eighteen carbon atoms, and more specifically from ten to sixteen carbon atoms. In certain embodiments, $R_3$ is —$R_4OSO_3^-$, —$R_4OR_5SO_3^-$, or —$OR_5SO_3^-$, and most preferably $R_3$ is —$CH_2O(CH_2)_3SO_3^-$ or —$CH_2O(CH_2)_4SO_3^-$. In certain embodiments, $R_4$ and $R_5$ are each, independently, an alkyl group having from one to eight carbons, more specifically from two to six carbon atoms, and more specifically, three or four carbon atoms.

In another embodiment, the anionic surfactants of the invention have the structure of general formula (Formula II):

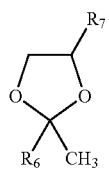

(II)

in which $R_6$ is alkyl;

$R_7$ is selected from $-OSO_3^-$, $-R_4OSO_3^-$, $-R_4OR_5SO_3^-$, and $-OR_5SO_3^-$, wherein $R_4$ and $R_5$ are each, independently, lower alkyl.

In certain embodiments, the surfactants of the present invention have the structure of Formula II, with the proviso that when $R_6$ is $-C_9H_{19}$, $-C_{11}H_{23}$, or $-C_{13}H_{27}$, $R_7$ is not $-CH_2O(CH_2)_4SO_3^-$.

In particular embodiments, the surfactant of the invention has the following chemical structure:

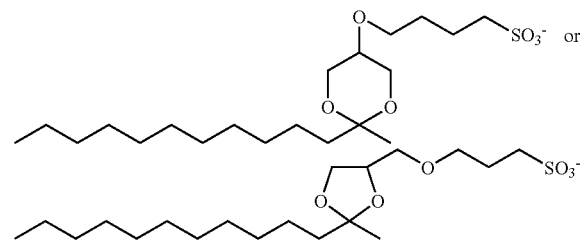

As indicated in more detail in the Examples, the methods of synthesis of the present invention produce isomers. Although the methods of using surfactants of the invention do not require separation of these isomers, such separation may be accomplished, if desired, by methods known in the art. For example, preparative high performance liquid chromatography methods may be used for isomer purification.

Methods of the Invention

The surfactants of the present invention may be used in applications that benefit from the initial presence and ultimate removal of a surfactant. In particular, the present invention is useful for methods for enhancing chemical reactions of molecules, e.g., biomolecules, with destructible surfactants. The chemical reactions may involve and/or be associated with analysis, e.g., solubilizing, separating, purifying, detecting and/or characterizing the molecules.

Accordingly, one embodiment of the invention provides a method for enhancing a chemical reaction of a molecule comprising contacting the molecule with a surfactant of the present invention to thereby enhance the chemical reaction of the molecule.

In another embodiment, the invention is a kit for enhancing a chemical reaction of a molecule comprising a surfactant of the present invention and instructions for use.

Yet another embodiment is directed to a method for analysis of a biomolecule comprising enhancing a chemical reaction of the biomolecule by contacting a sample containing the biomolecule with a surfactant of the present invention and analyzing the sample to thereby analyze the biomolecule.

In certain embodiments of the invention, the molecule is a biomolecule. In addition, the biomolecule may be contained in a biological sample, for example, inclusion bodies, biological fluids, biological tissues, biological matrices, embedded tissue samples, or cell culture supernatants. Examples of biomolecules include peptides and proteins, e.g., lipophilic proteins, receptors, membrane-bound proteins, or proteolytic proteins.

In certain embodiments, the method for enhancing a chemical reaction may additionally comprise an analysis of the molecule, e.g., following the chemical reaction. Moreover, analysis of the molecule, e.g., biomolecule, following the chemical reaction, may include, but is not limited to, solid phase extraction; solid phase micro extraction; electrophoresis, capillary electrophoresis or gel electrophoresis, e.g., polyacrylamide gel electrophoresis, e.g., tube, slab gel or capillary formats, free zone electrophoresis; mass spectrometry, e.g., MALDI-MS or ESI; liquid chromatography, e.g., high performance, e.g., reverse phase, normal phase, or size exclusion, ion-pair liquid chromatography; liquid-liquid extraction, e.g., accelerated fluid extraction; supercritical fluid extraction; microwave-assisted extraction; membrane extraction; soxhlet extraction; precipitation; electrochemical detection; staining; elemental analysis; Edmund degradation; ultraviolet detection; clarification; nuclear magnetic resonance; infrared analysis; flow injection analysis; capillary electrochromatography; and combinations thereof. In specific embodiments, the analysis further comprises separating the resulting biomolecule fragments.

In certain embodiments, the mass spectrometry analysis is surface desorption ionization (SDI) mass spectrometry. Although removal of the degraded surfactant is easily accomplished, it is not required for SDI-MS. In fact, in SDI-MS analysis, degradation of the surfactant is not required prior to analysis. In this regard, mass spectrometric analysis has shown that a 250 fmol ACTH sample spotted with 0.25% surfactant of the invention onto a MALDI surface gave virtually the same signal intensity and quality as when the sample was applied without surfactant. Furthermore, although degradation is required for electrospray ionization mass spectrometry, it is not necessary to remove the degraded surfactant prior to analysis.

The chemical reaction involving the molecule may include chemical digestion, chemical alteration, or a combination thereof. Moreover, the chemical reaction with the molecule, e.g., biomolecule, or analysis of the molecule may involve denaturation, solubilization, or a combination thereof. Additionally, in certain embodiments the enhancement of the chemical reaction facilitates on-line automation, separation, mass spectrometric analysis, or a combination thereof. Furthermore, the chemical reaction may also be performed under microscale conditions, e.g., reactions may performed within the spot used for SDI analysis. After the chemical reaction proceeds, the surfactant of the present invention involved in enhancing the chemical reaction can be degraded, e.g., by contact with an acidic solution. For example, sodium 4-[(2-methyl-2 undecyl-1,3-dioxolan-4-yl)methyl]-1-propanesulfonate (ALS), the synthesis of which is shown in Example 1, while stable at pH 7-8 (suitable pH for trypsin digestion), may be degraded at low pH:

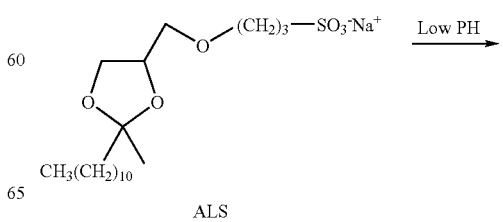

ALS

-continued

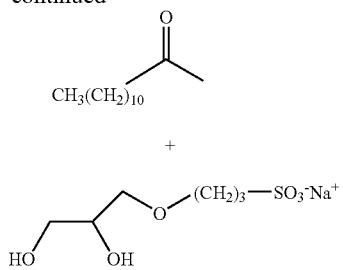

In particular embodiments, the chemical reaction using surfactants of the present invention is chemical digestion. In one embodiment, the chemical digestion occurs by contacting a molecule, e.g., a biomolecule, with a protease. Exemplary proteases include, but are not limited to specific proteases such as Trypsin, Chymotrypsin Lys-C, Glu-C (V8 protease), AspN, Arg-C, S. Aureus, and Clostripain, and non-specific proteases, such as, Pepsin, and Papain. In certain embodiments of the invention the protease is immobilized, e.g., immobilized enzymatic reactor. Alternatively, digestion may be accomplished by reaction with CNBr or reaction with hydroxylamine. Additionally, in certain embodiments of the invention, the digestion can occur in an electrophoretic gel in the presence or absence of one or more surfactants that are different from the surfactants of the invention, e.g., SDS.

Solubilization of insoluble samples by surfactants of the present invention allows digestion of samples that are typically insoluble and therefore difficult to digest by known methodology. In addition, the surfactants of the present invention enable the use of lower amounts of trypsin to digest a protein. For example, the ratio of trypsin to total protein is typically 1:50 to 1:20. However, in the presence of the surfactants of the present invention, the ratio of trypsin to total protein can be 1:100 or lower. Moreover, the use of the surfactants of the invention, for example, enables rapid tryptic digestion without a concomitant increase in miscleavages, as observed for known methodologies, e.g., addition of organic solvent or heat.

Alternatively, the chemical reaction using surfactants of the present invention is chemical alteration. Exemplary chemical alterations include, but are not limited to, alkylation, reduction, e.g., using DTT, and a combination thereof. In fact, the surfactants of the invention, unlike the organic salts, such as urea and detergents, e.g., SDS, used for solubilization prior to reduction and allylation do not inhibit the activity of proteases, e.g., trypsin. Therefore, in certain embodiments the resulting reaction mixtures require no additional sample preparation steps prior to in-solution digestion.

Additionally, it is known that if digestion, in which urea has been utilized as a solubilizing agent, is allowed to proceed for too long, the urea will act upon and modify the protein, making analysis of peptide fragments more difficult. In this regard, the surfactants of the invention will not modify the protein, regardless of the length of time allowed for digestion.

In certain embodiments, the enhancement of the chemical reaction comprises a favorable chemical property. Exemplary favorable chemical properties include, without limitation, a more complete reaction, increased efficiency, increased yield, increased rate, and increased utility.

Figure 6A:
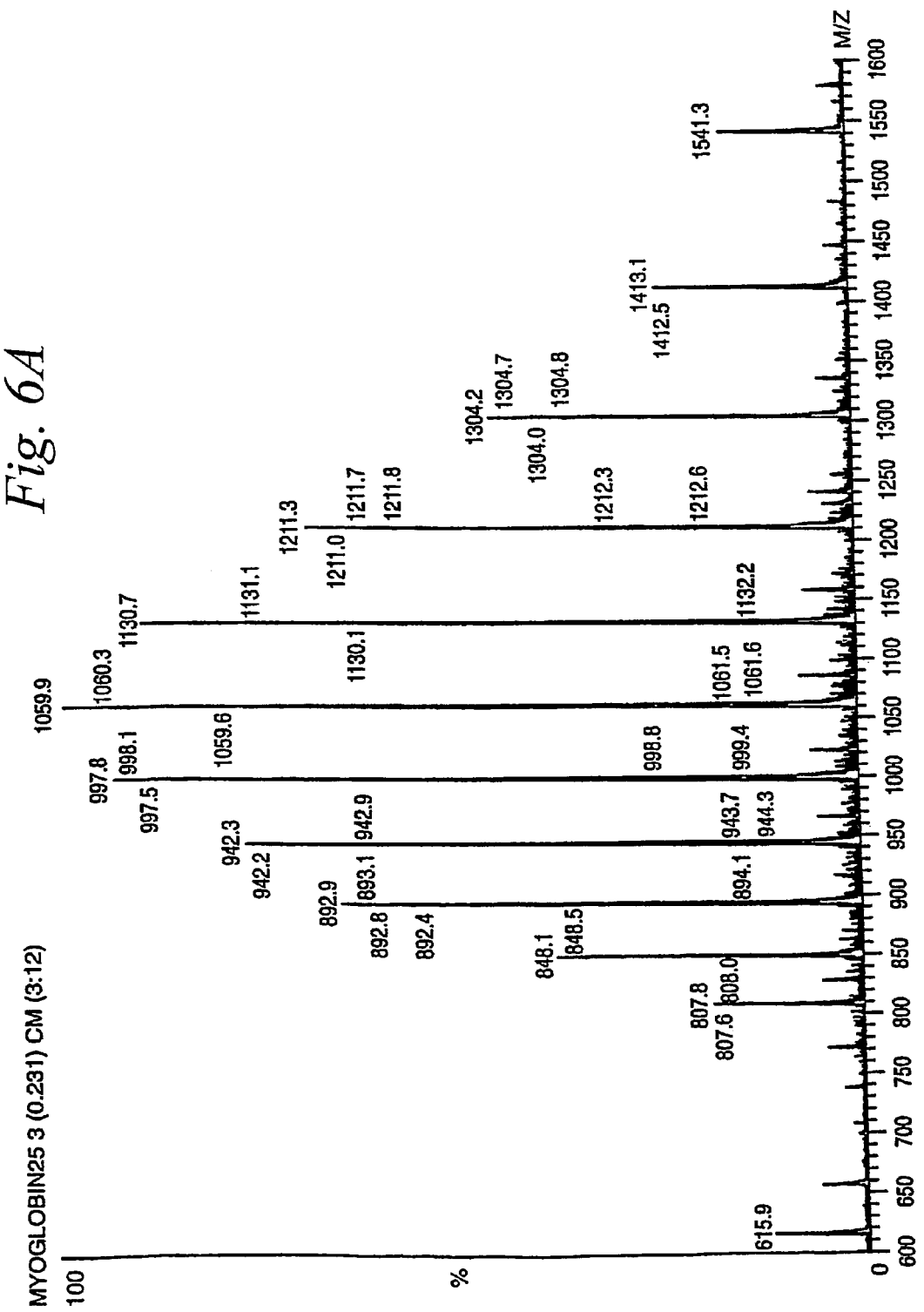
FIGS. 6A-6C show electrospray mass spectra of myoglobin under the various treatment conditions described in Example 7.
Figure 6B:
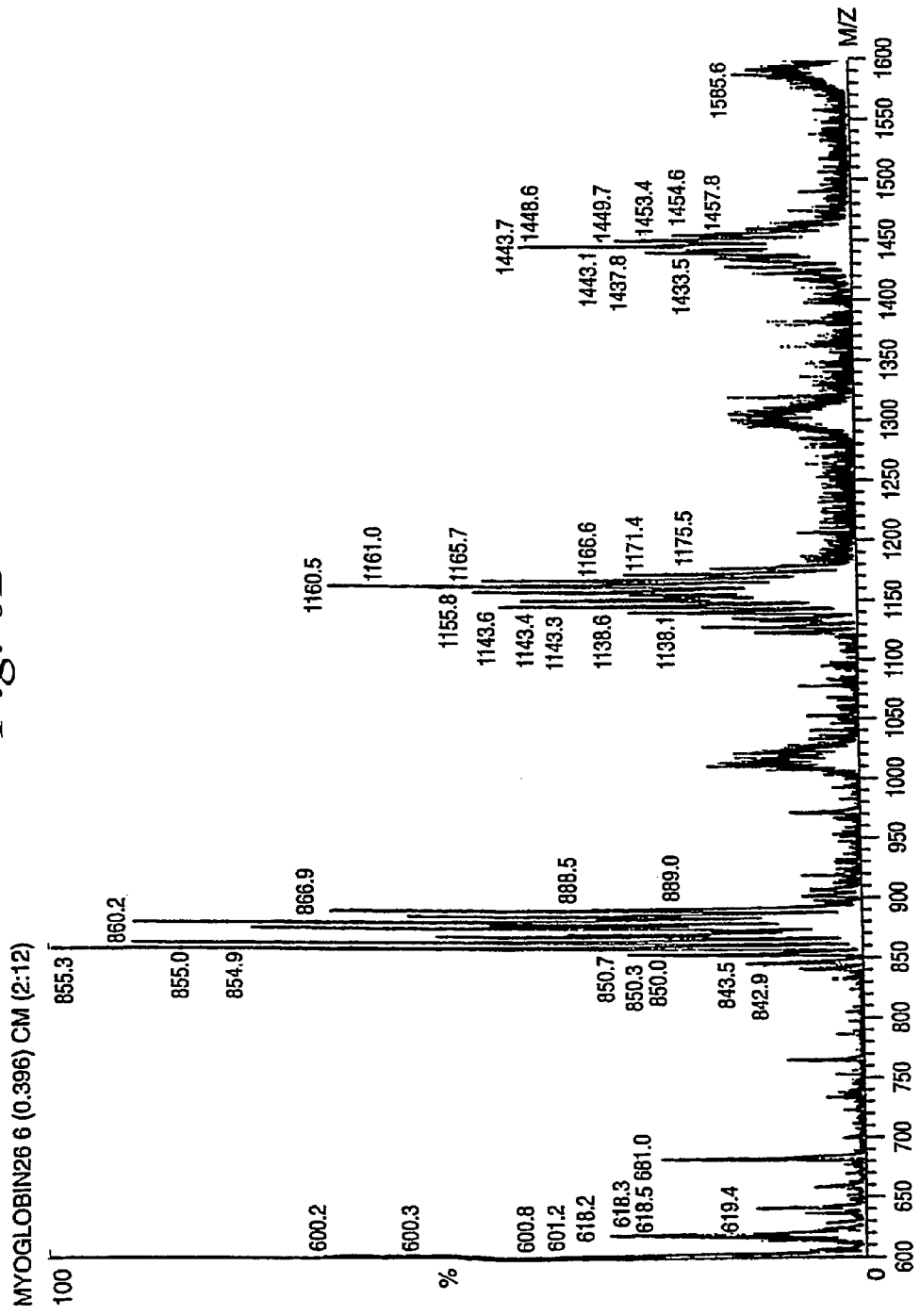
Figure 6C:
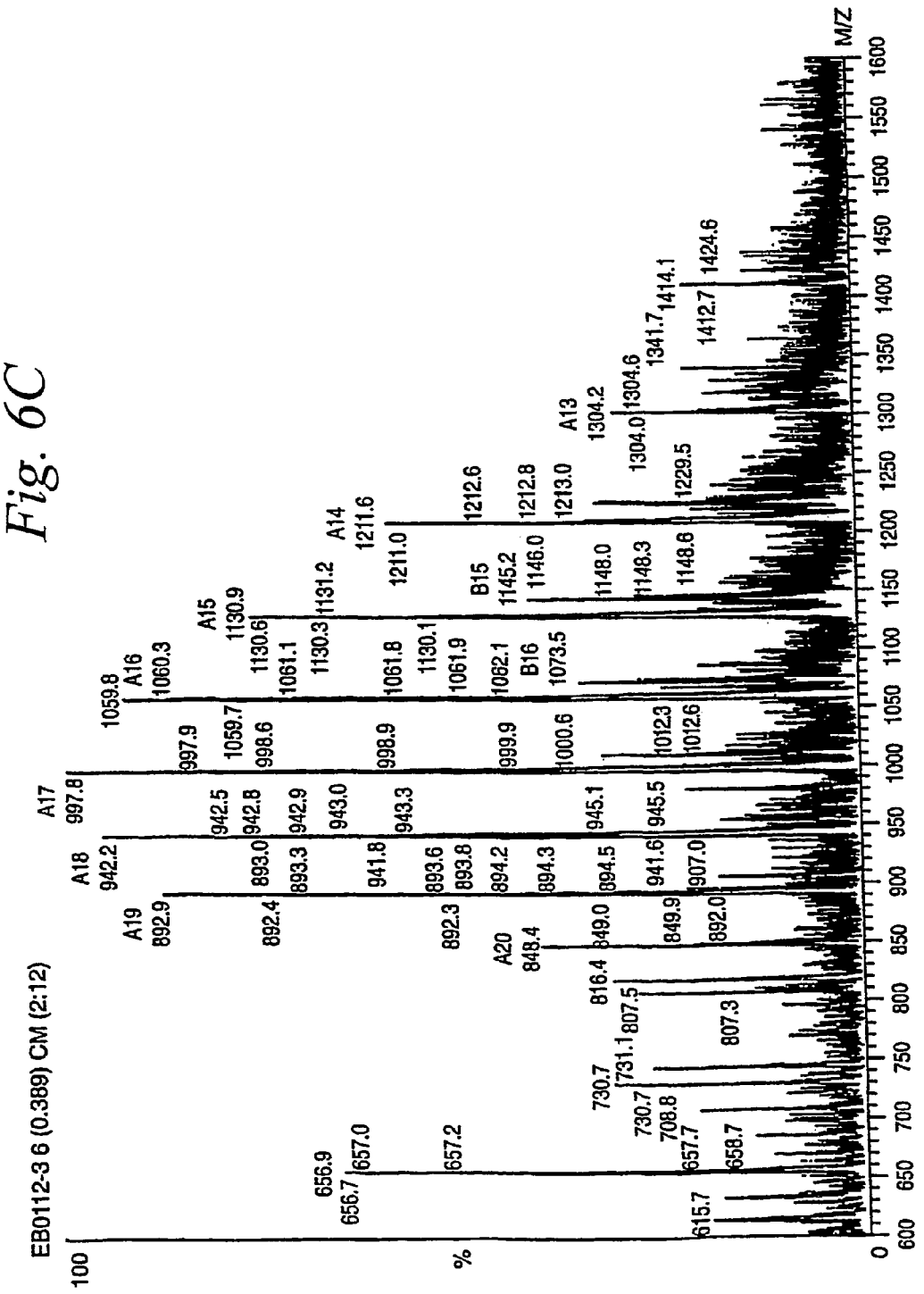

The sensitivity of mass spectrometric detection of proteins in the presence of degraded ALS is much greater than in the presence of SDS. The anionic surfactants of the present invention provide surprising advantages over SDS when analyzing molecules. For example, in FIG. 6B, which depicts the mass spectrum of myoglobin treated with SDS, no signals due to myoglobin are observed. In contrast, FIG. 6C shows the mass spectrum of myoglobin treated with a surfactant of the present invention, after degradation, exhibits a strong myoglobin signal. Without wishing to be bound by any particular theory, this result is believed to be due to at least two effects: 1) few, if any, micelles are present with the degraded surfactant of the present invention; and 2) fewer adducts of sample and the degraded surfactant of the invention are formed. These effects allow better sensitivity in mass spectrometry than is possible when SDS is used.

After the chemical reaction, the molecules are released from the surfactants of the present invention by degradation with acidic solution. The molecules may be further purified by conventional separation methods such as liquid-liquid extraction, solid-phase extraction or liquid chromatography. This ability to separate the molecules from surfactants easily after the chemical reaction may be used in various applications, with significant benefits to separation science.

An additional embodiment of the invention provides a method for enhancing chemical digestion of a biomolecule comprising contacting the molecule with a digestive enzyme, e.g., a protease, and a surfactant of the present invention, to thereby enhance the chemical digestion of the molecule. In an additional embodiment, the invention provides a kit for enhancing chemical digestion of a biomolecule comprising a surfactant of the present invention, and instructions for use. In certain embodiments, the biomolecule is a protein. Exemplary proteins include, but are not limited to, bovine serum albumin, lysozyme, ovalbumine, myoglobin, ubiqutin, and bacteriorhodopsin. In certain embodiments, the kit for enhancing chemical digestion of a biomolecule further comprises a digestive enzyme, e.g., a protease. Exemplary proteases include, without limitation, Trypsin, Chymotrypsin Lys-C, Glu-C (V8 protease), AspN, Arg-C, S. Aureus, Clostripain, Pepsin, and Papain.

In another embodiment, the invention provides a method of capturing a lipophilic compound comprising contacting a lipophilic compound with a surfactant of the present invention, and degrading the surfactant to produce hydrophobic compound, e.g., by contact with an acidic solution, to thereby capture the lipophilic compound. The lipophilic compound may be contained in a sample, e.g., a biological sample. In certain embodiments, the product of degradation is compatible with mass spectrometric detection, high performance liquid chromatography analysis, and with protease activity. In addition, the lipophilic compound can be a protein fragment or peptide. In certain embodiments, the protein fragment is generated by chemical digestion or a combination of chemical alteration and chemical digestion. In specific embodiments of the invention, the protein fragment or the peptide is the product of a protein that has been digested by contact with a protease and a surfactant of the present invention.

Another embodiment of the invention provides a method for enhancing surface desorption ionization analysis, e.g., MAUI-MS, DIOS, or SELDI, of a molecule, e.g., a biomolecule, comprising solubilizing a molecule by contacting the molecule with a surfactant of the present invention, to thereby analyze the sample by surface desorption ionization. The surfactant can be degraded prior to analysis, but the degradation is not required. Therefore, in certain embodiments of the invention, the surfactant is degraded prior to analysis, while in other embodiments of the invention the surfactant is not degraded prior to analysis.

In addition, better recoveries are expected for hydrophobic proteins or proteins that are proteolysis resistant. Analysis of a complex mixture may be difficult due to the large number of peptide fragments. Having a way to reduce the number of fragments by fractionating a small percentage of them could provide some benefit. Additionally, once the sample is segregated into two distinct classes, the HPLC separation can be optimized for each resulting class of peptides, thereby potentially resulting in additional information.

In another embodiment, SDS that has bound to the proteins during SDS-PAGE can be replaced with the surfactants of the invention by washing with buffers containing a surfactant of the invention, e.g., ALS.

EXEMPLIFICATION

Example 1

Preparation of sodium 4-[(2-methyl-2 undecyl-1,3-dioxolan-4-yl)methyl]-1-propanesulfonate(3,4) [ALS]

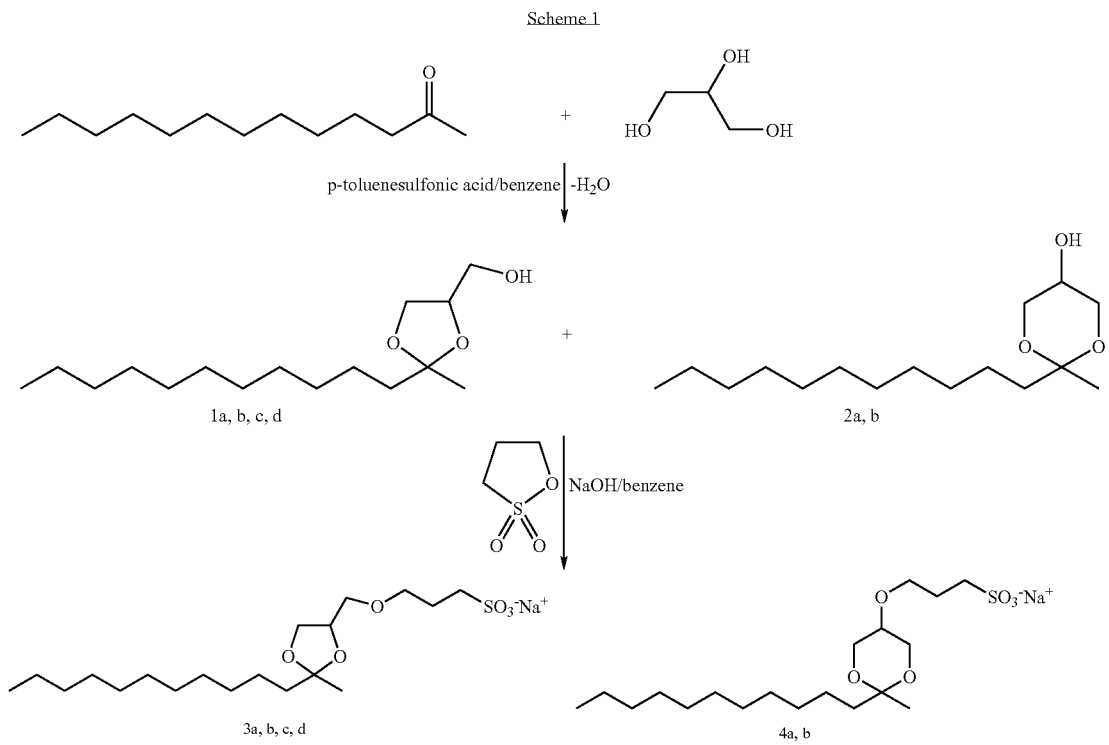

Scheme 1

This example describes the preparation of certain anionic surfactants of the present invention. Various modifications to the following procedures will be routine to one of ordinary skill in the art, in light of the teachings herein. For example, in the following procedures, toluene may be substituted for benzene. In addition, any solvent that provides a sufficient yield may be used in the recrystallization step.

1. Synthesis of 4 hydroxymethyl-2-methyl-2-undecyl-1,3-dioxolane (1, 2)

Firstly, 100 g (0.5 mol) of 2-tridecanone (Aldrich P/N 17,283-9), 56 g (0.6 mol) of glycerol (Aldrich P/N 32,00-5), 200 mL of benzene, and 1.8 grams of p-toluenesulfonic acid (Aldrich P/N 40,2885) were placed in a 500 mL round bottom flask fitted with a Dean Stark apparatus. The mixture was heated to reflux with stirring until no further separation of water appeared. The reaction mixture was cooled to room temperature and washed successively with a 100 mL portion of 5% sodium carbonate solution and three 100 mL portions of water. The organic layer was dried over sodium sulfate, filtered and the benzene was removed with a rotary evaporator. The residual oil was fractionated by distillation under reduced pressure to give the desired product (b.p. 140° C./0.3 mm Hg). The identity of the product was confirmed by $^1$H NMR in CDCl$_3$.

2. Synthesis of ALS 50 g (0.18 mol) of 4-hydroxymethyl-2 methyl-2 undecyl-1,3-dioxolane, 8 g (0.2 mol) of powdered sodium hydroxide and 200 mL of benzene were placed in a 4 neck 500 mL flask fitted with a condenser, mechanical stirrer and a thermometer. The suspension was stirred at a constant 50° C. while 25 g (0.2 mol) of 1,3-propanesultone (Aldrich P/N P5,070-6) was slowly added over 30 minutes. The suspension was then stirred at 70-75° C. for at least 6 hours. Upon completion, the reaction mixture was poured into 500 mL of boiling ethanol. The volume of the resulting mixture was then reduced in vacuo with a rotary evaporator, producing a solid residue that was subsequently dissolved in boiling ethanol and hot filtered.

The solid residue was additionally extracted with boiling ethanol, which was combined with the mother liquor. The solvent was removed in a rotary evaporator, and the resulting residue was then recrystallized from ethanol to yield the product. Identity of the product was confirmed by $^1$H NMR in D$_2$O.

Example 2

Trypsin Activity Assay

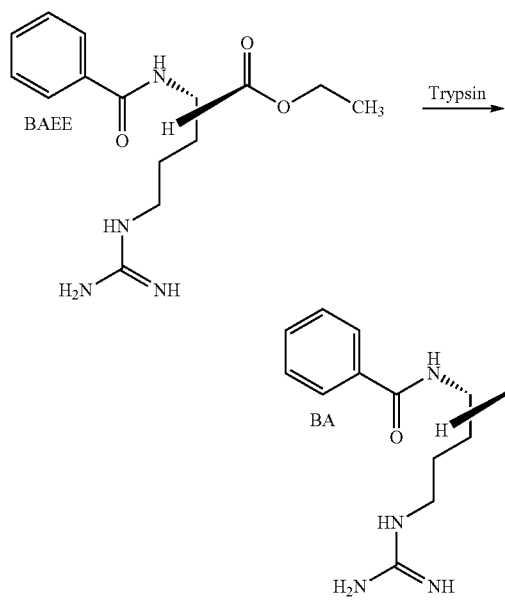

Trypsin activity measurements were carried out by introducing 1 μg/ml of trypsin to 0.25 mM N-α-benzoyl-L-arginine ethyl ester (BABE, pH 7.9) at room temperature. Changes in trypsin activity were plotted by measuring the rate of hydrolysis of BAEE to a UV active product, BA, at A 252 nm. The analysis, shown in FIG. 1 and Table 1, indicates that SDS inhibits trypsin activity at each the percentages examined. However, the addition of ALS to the trypsin solution containing SDS, shows an increase in trypsin activity, indicating a reactivation of trypsin digestion within the solution.

TABLE 1

| Trypsin Activity Summary | |
| --- | --- |
| Trypsin solution * | Trypsin activity (%) ** |
| No additive | 100 |
| 0.1% ALS | 99 |
| 0.5% ALS | 87 |
| 0.1% SDS | 20 |
| 0.5% SDS | 1 |
| 0.1% SDS/0.1% ALS | 58 |
| 50% Methanol | 31 |
| 50% Acetonitrile | 92 |
| 2M Urea | 85 |
| 4M Urea | 71 |

\* 0.5 μg of trypsin in 50 mM ammonium bicarbonate, pH 7.9; 0.2 mM of BEAA
\*\* Measured as delta BEAA absorbance @253 (slope within 5 min)

Example 3

Trypsin Digestion of Various Proteins

Proteins (2-20 μM), indicated in Table 2, were solubilized in 50 mM $NH_4HCO_3$ or 0.1-0.25% (w/w) ALS before tryptic digestion. The trypsin to protein ratio used was 1-2%. The protein (~17 μM) was solubilized with 8M urea or 0.25% ALS. After tryptic digestion, ALS was destroyed rapidly by addition of strong acid such as HCl or TFA. The by-products were removed by centrifugation prior to MS analysis. Protein digests were mass analyzed either by a MALDI-TOF mass spectrometer (M@LDI™ LR, Micromass UK Ltd) or separated by RP-HPLC (CapLC®, Waters Corporation) then interfaced to an orthogonal acceleration TOF mass spectrometer (LCT™, Micromass UK Ltd) via an electrospray ionization source.

Figure 2A:
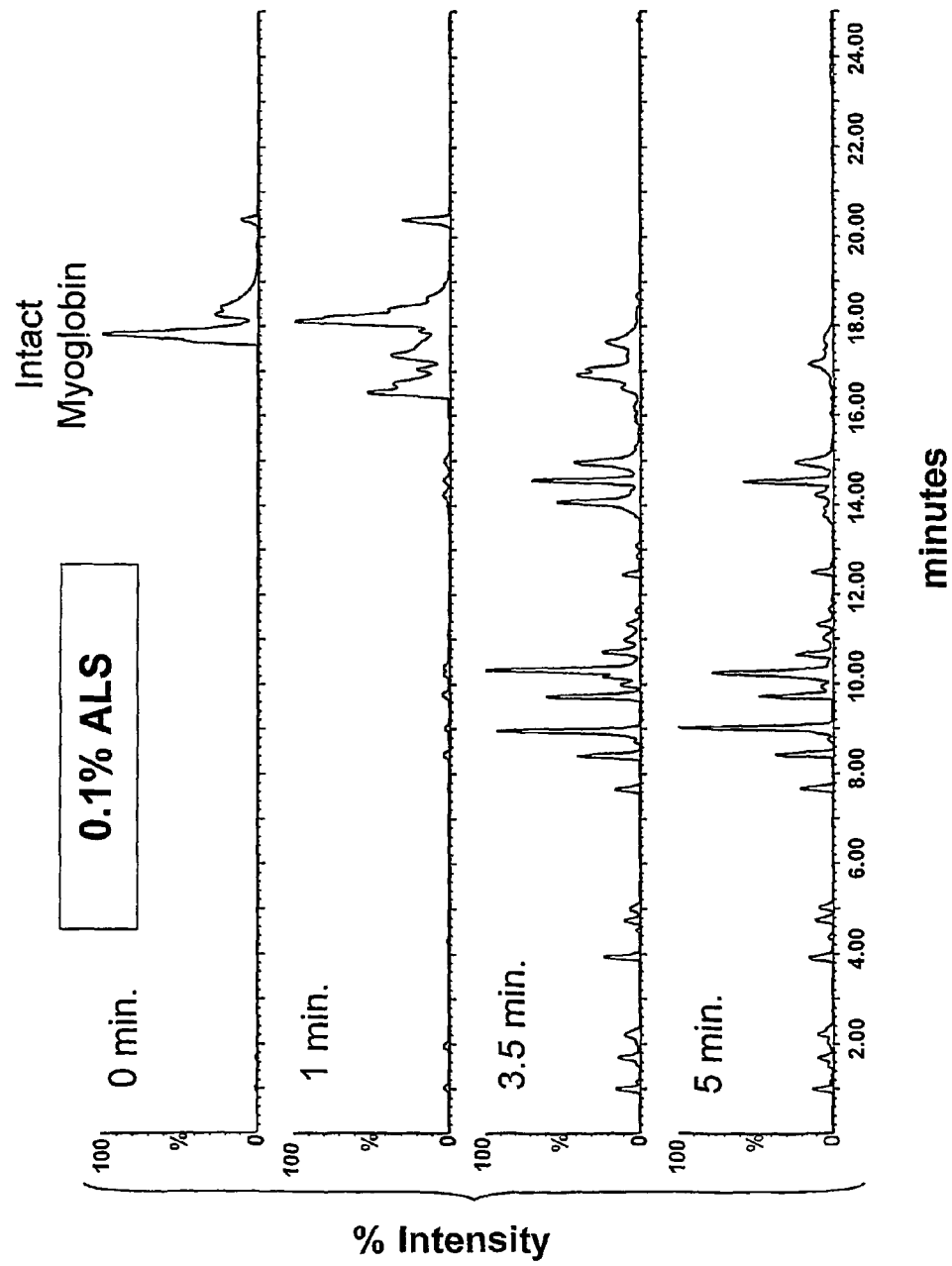

FIG. 2 shows the LC/MS TIC of tryptic digested myoglobin solubilized with (A) 0.1% ALS or (B) 50 mM $NH_4HCO_3$ (no ALS). Myoglobin treated with 0.1% ALS was observed to undergo complete tryptic digestion within 5 minutes. Myoglobin in 50 mM $NH_4HCO_3$ was resistant to tryptic digestion. In fact, a majority of myoglobin in the sample without ALS remained undigested after 9 hrs.

Figure 3A:
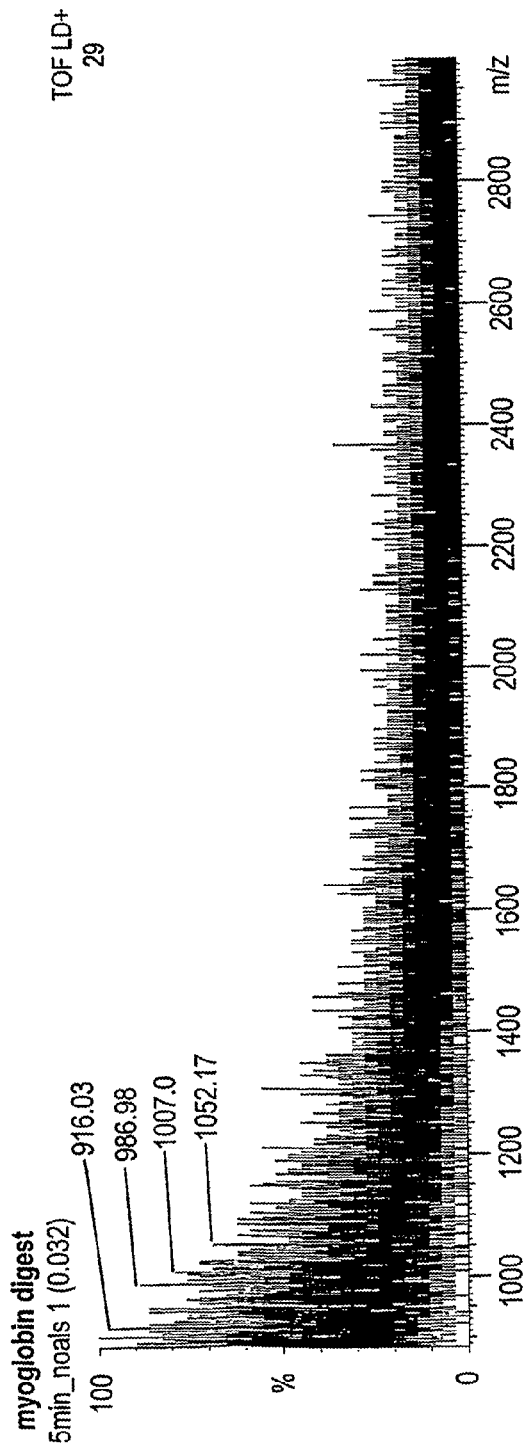
FIGS. 3A-3B show the MALDI-TOF mass spectrometry analysis of the tryptic digestion of myoglobin after 5 minutes solubilized with 0.1% ALS or 50 mM $NH_4HCO_3$ (no ALS).
Figure 3B:
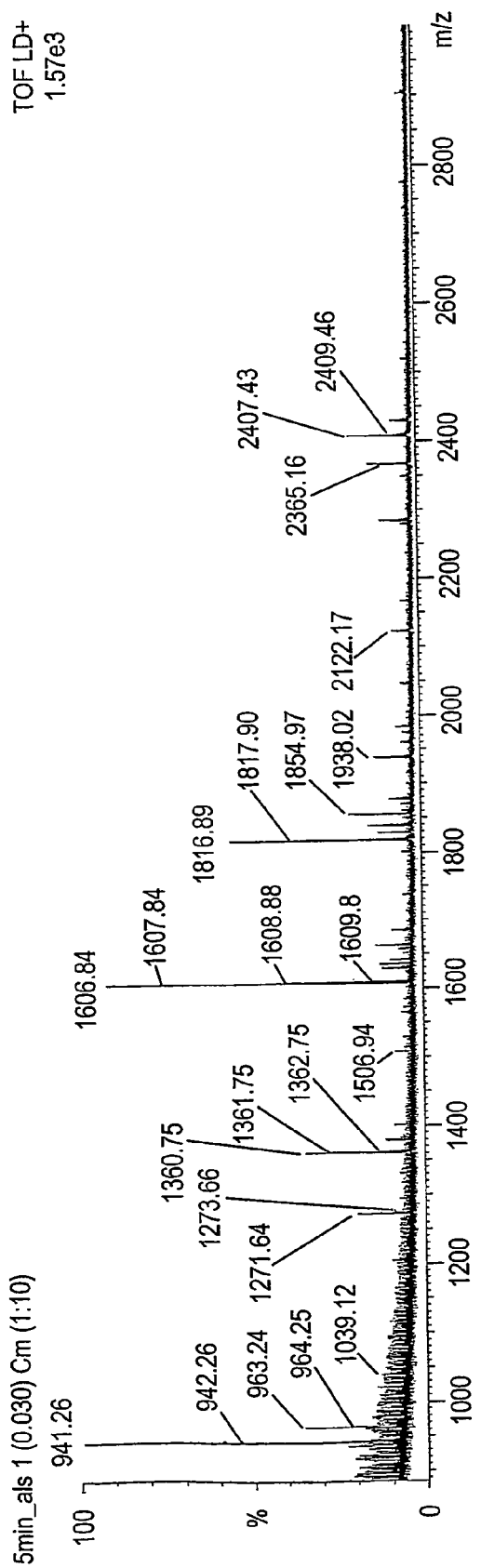

In addition, MALDI-TOF mass spectrometry was also performed on the digested sample, prior to degradation of the surfactant (i.e., before addition of acid). FIG. 3 shows the MALDI-TOF mass spectrometry analysis of the tryptic digestion of myoglobin after 5 minutes solubilized with 0.1% ALS or 50 mM $NH_4HCO_3$ (no ALS).

TABLE 2

| Protein Digestion by Trypsin | | | | | |
| --- | --- | --- | --- | --- | --- |
| Protein | Digestion Difficulty | w/o ALS | | With ALS(0.1%) | |
| BSA (66 K) | Easy | minutes | 16 peptides 1+ intact protein | minutes | 21 peptides |
| Lysozyme (16K) | Easy | minutes | 2 peptides + intact protein | minutes | 6 peptides |
| Ovalbumine (43 K) | Moderate | minutes | 0 peptides + intact protein | minutes | 2 peptides |
| Myoglobin (17 K) | Moderate | minutes | 0 peptides + intact protein | minutes | 12 peptides |
| Ubiqutin (8 K) | Difficult | minutes | 0 peptides + intact protein | minutes | 9 peptides |
| Bacteriorhodopsin (26 K) | Very Difficult | Overnight | 1 peptide (weak signal) + intact protein | Overnight | 3 peptides |

\*Proteins are not reduced
\*MALDI-TOF (900-3000 amu)

Direct Analysis of Sample, No Work Up (No ZipTip™)

Furthermore, Table 2 indicates not only was the rate digestion enhanced, but also, more complete, in that the number of peptide fragments generated was significantly increased.

Example 4

Comparative Digestion of Myoglobin with Various Proteases

Figure 4A:
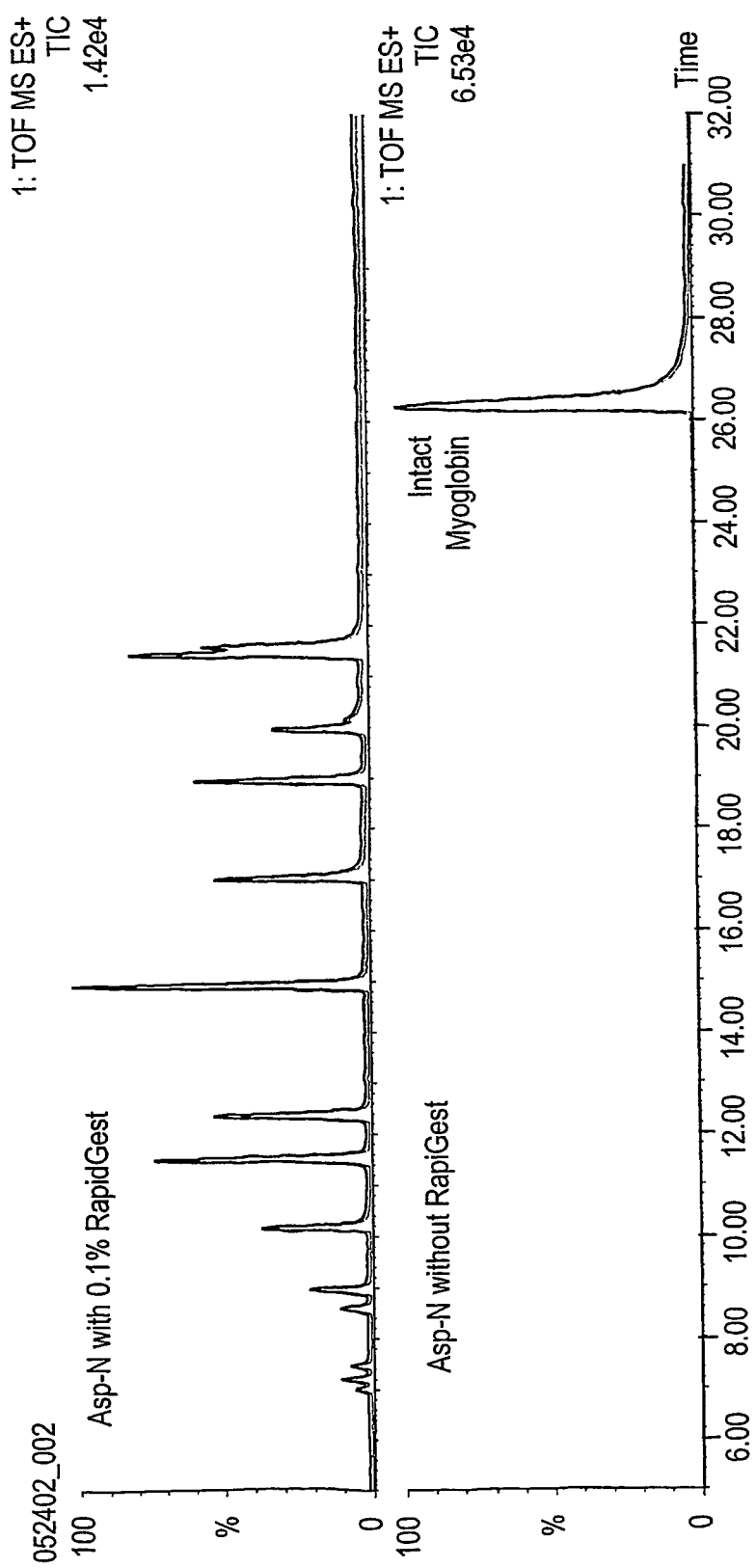
FIGS. 4A-4C show the mass spectra of the myoglobin comparative digestion (in the presence and absence of ALS), using (4A) Asp-N, (4B) Lys-C, and (4C) Glu-C performed in Example 4.
Figure 4B:
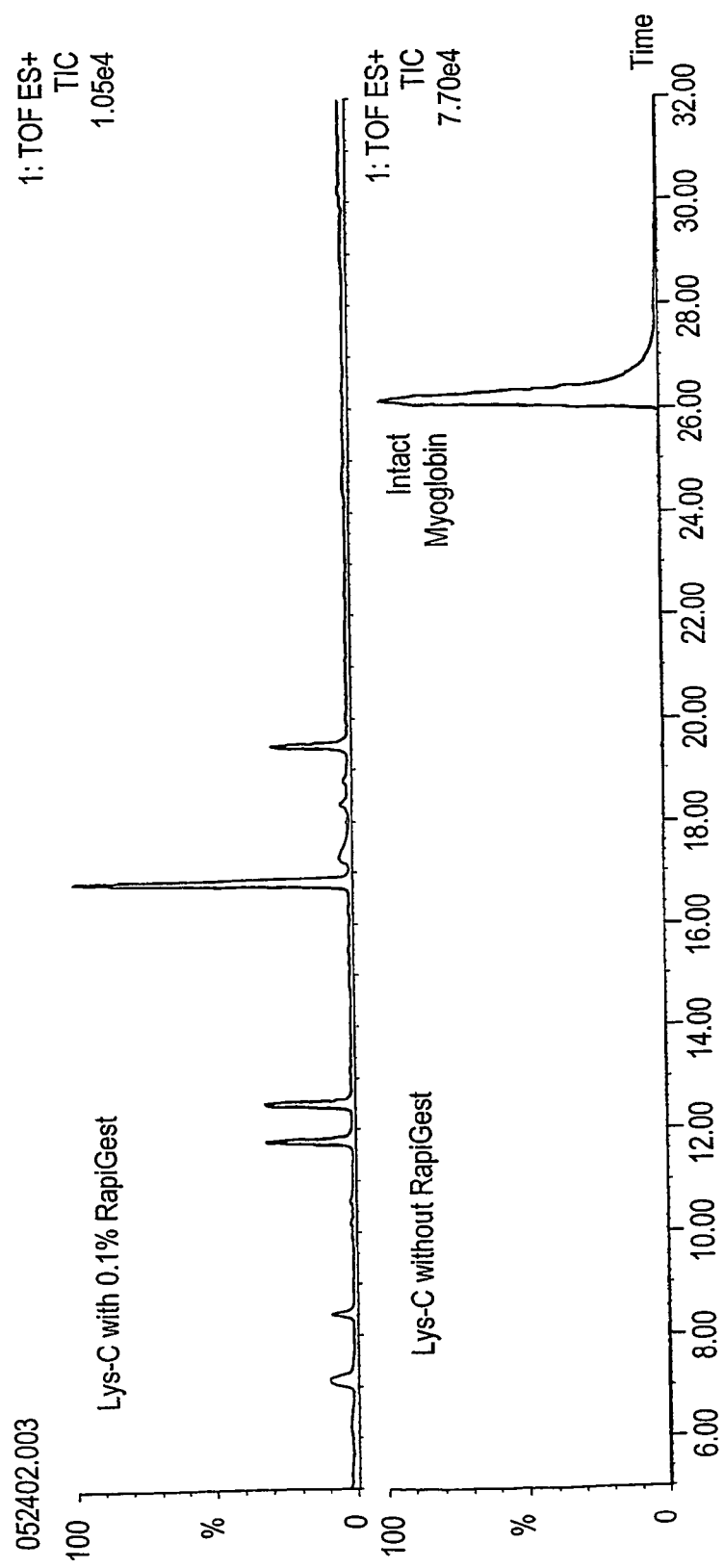
Figure 4C:
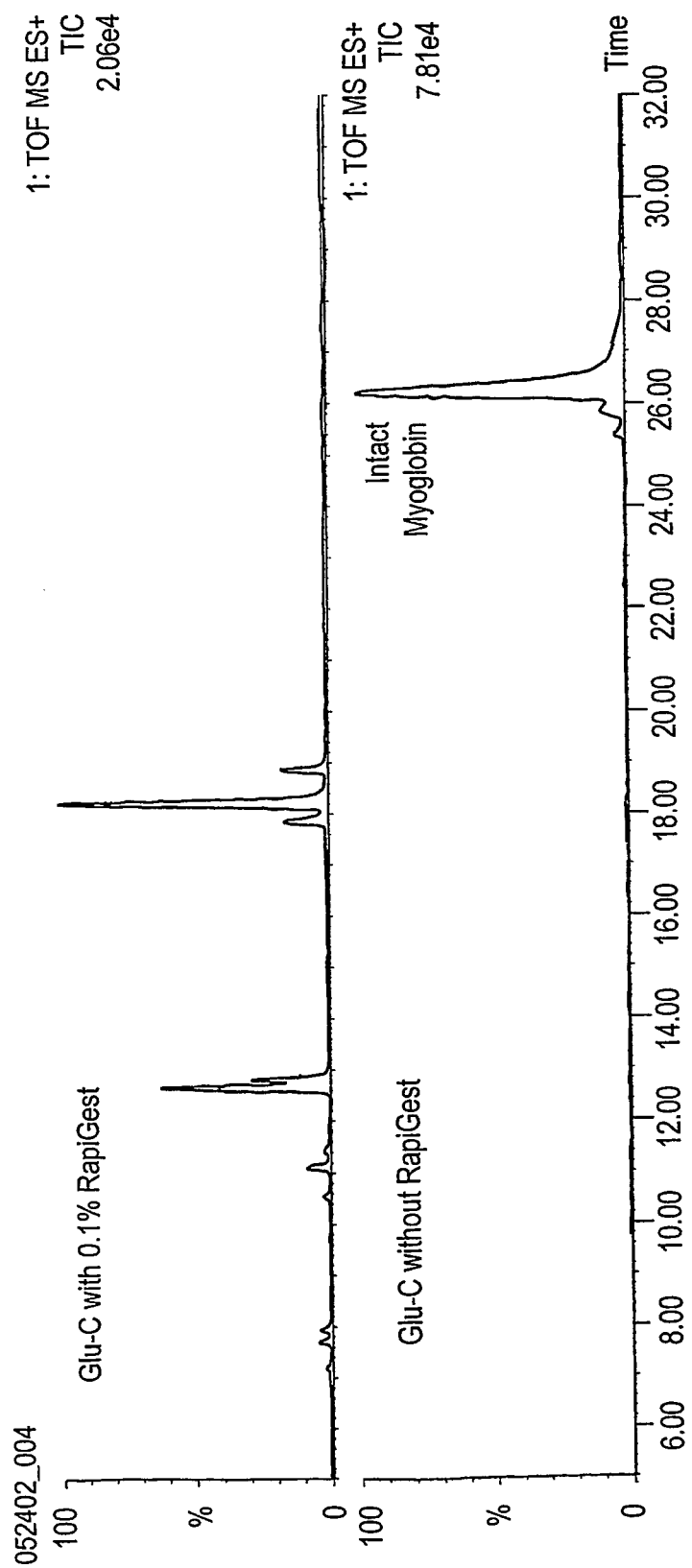

Myoglobin comparative digestion was performed as in Example 3 (in the presence and absence of ALS), with the exchange of the following proteases for trypsin:
A. Asp-N (FIG. 4A)
B. Lys-C (FIG. 4B)
C. Glu-C (FIG. 4C)
Digestions were performed for about 50 minutes. The enzymes were purchased from Roche Diagnostics. Analysis is shown in FIGS. 4A-4C, as indicated above. In each case, when no ALS was in the digestion solution, no observable digestion took place. However, with ALS, within about 50 minutes, the entire protein was consumed.

Example 5

In Solution Protein Digestion Using Immobilized Trypsin

Trypsin immobilized on agarose beads may be purchased from Pierce. The beads (100 μl, 20 units of enzyme activity) is pipetted into a vial and is washed with 50 mM ammonium acetate. The excess buffer is then removed, followed by the addition of 100 μg of Myoglobin dissolved in 100 μl of 50 mM ammonium acetate buffer, pH ~7.9. The reaction mixture is mixed vigorously for 5 minutes, the vial is briefly centrifuged to separate beads from solution, and the clear liquid is then used for analysis. MS and HPLC are used to monitor the content of myoglobin and generated peptides.

This experiment is then repeated with an addition of ALS to the reaction solution. Final concentration of ALS was 0.1% (w/v). The rate of enzymatic reaction is compared with the experiment performed in the absence of ALS.

Example 6

On-Line Protein Digestion Using Trypsin Reactor

Trypsin immobilized on agarose beads may be purchased from Pierce. Flow-through devices may be constructed in order to demonstrate on-line protein digestion.

A gel loading tip is crimped at the bottom and is filled with slurry of agarose beads with immobilized trypsin. The excess liquid (50% glycerol, 0.05% sodium azide) can then removed while the beads are entrapped in the tip. The length of the bead is ~2 centimeters.

The tip is then filled from the top with an excess of 50 mM ammonium acetate buffer and is washed several times using moderate positive pressure generated by pipette or by centrifugation. Myoglobin (100 μg) is dissolved in 100 μl of 50 mM ammonium acetate buffer, pH ~7.9 is placed on top of the beads layer and slowly is passed through the bead using either positive pressure or low speed centrifugation. The experiment is complete within 30 seconds. The solution is collected into a reservoir and analyzed off-line by MS and HPLC.
On-Line Setup This experiment is then repeated using similar setup with 100 μg of Myoglobin dissolved in 100 μl of 50 mM ammonium acetate buffer containing 0.1% ALS (w/v). The speed of digestion is compared to the control ALS free experiment.

The on-line setup is constructed using cartridge housing (e.g. 20×2.1 mm) packed with agarose beads with immobilized trypsin. The protein sample is then injected and is washed from the cartridge with 50 mM ammonium acetate buffer directly onto the analytical column packed with RP-HPLC sorbent. The trapped peptides are eluted from the main column while trypsin reactor is being washed and equilibrated with fresh ammonium acetate buffer.

Example 7

Mass Spectrometric Detection of Myoglobin Treated with ALS or SDS

In this example, mass spectroscopy is used to compare a surfactant of the present invention to SDS.

Mass spectrometric detection was performed on myoglobin using a Platform LC (Micromass, Manchester, UK) with constant infusion. A stock solution of 50 μM horse skeletal muscle myoglobin (Sigma P/N M0630) was prepared in 50/50 20 mM ammonium acetate, pH 5.1/acetonitrile (v/v). A stock solution of 1% SDS and 1% ALS were also prepared in both 50/50 ammonium acetate/acetonitrile, and 40/40/10 ammonium acetate/acetonitrile/glacial acetic acid. The surfactant stock solutions were both prepared fresh, and allowed to sit for at least 16 hours. To 100 μL of each of the surfactant stock solutions was added 100 μL of myoglobin stock and 800 μL 50/50 ammonium acetate/acetonitrile. Each solution was then drawn into a 1 mL syringe and placed in a syringe pump (Harvard Instruments). The solution was infused into the mass spectrometer at a flow rate of 20 μL/min. Mass spectrometer settings were as follows:

Gas flow rate: 340 L/h; Source temperature: 100° C., Capillary voltage: 3.46 kV; Cone voltage: 25 V; Ion energy: 0.6; Scan rate: 3.0 sec/scan; Scan range: 250-1600 amu. Mass spectra are shown in FIG. 6. For the case where SDS is the surfactant, no signals are observed which are due to myoglobin. The spectrum of the sample containing degraded ALS, on the other hand, exhibits a strong myoglobin signal.

Example 8

Mass Spectrometric of Disulfide Bond Reduction of Lysozyme with ALS

Figure 5A:
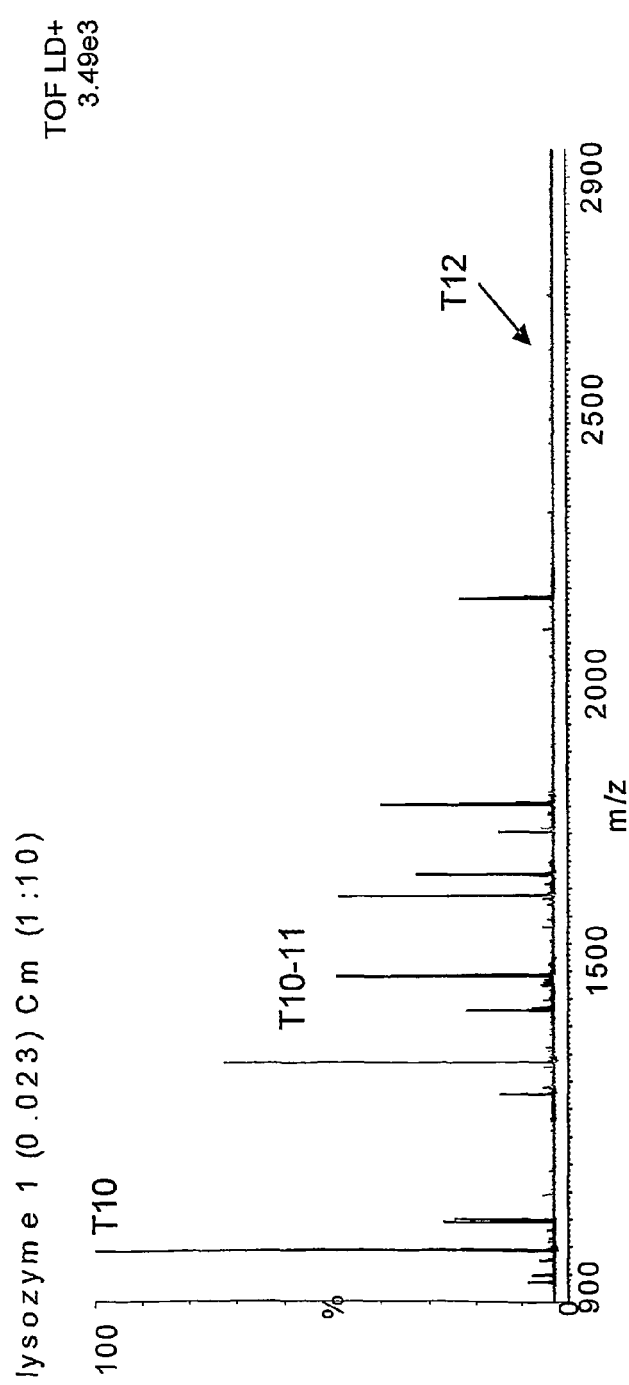
FIGS. 5A-5B show the mass spectrometry analysis of the disulfide bond reduction of lysozyme C in the presence and absence of 0.25% ALS.
Figure 5B:
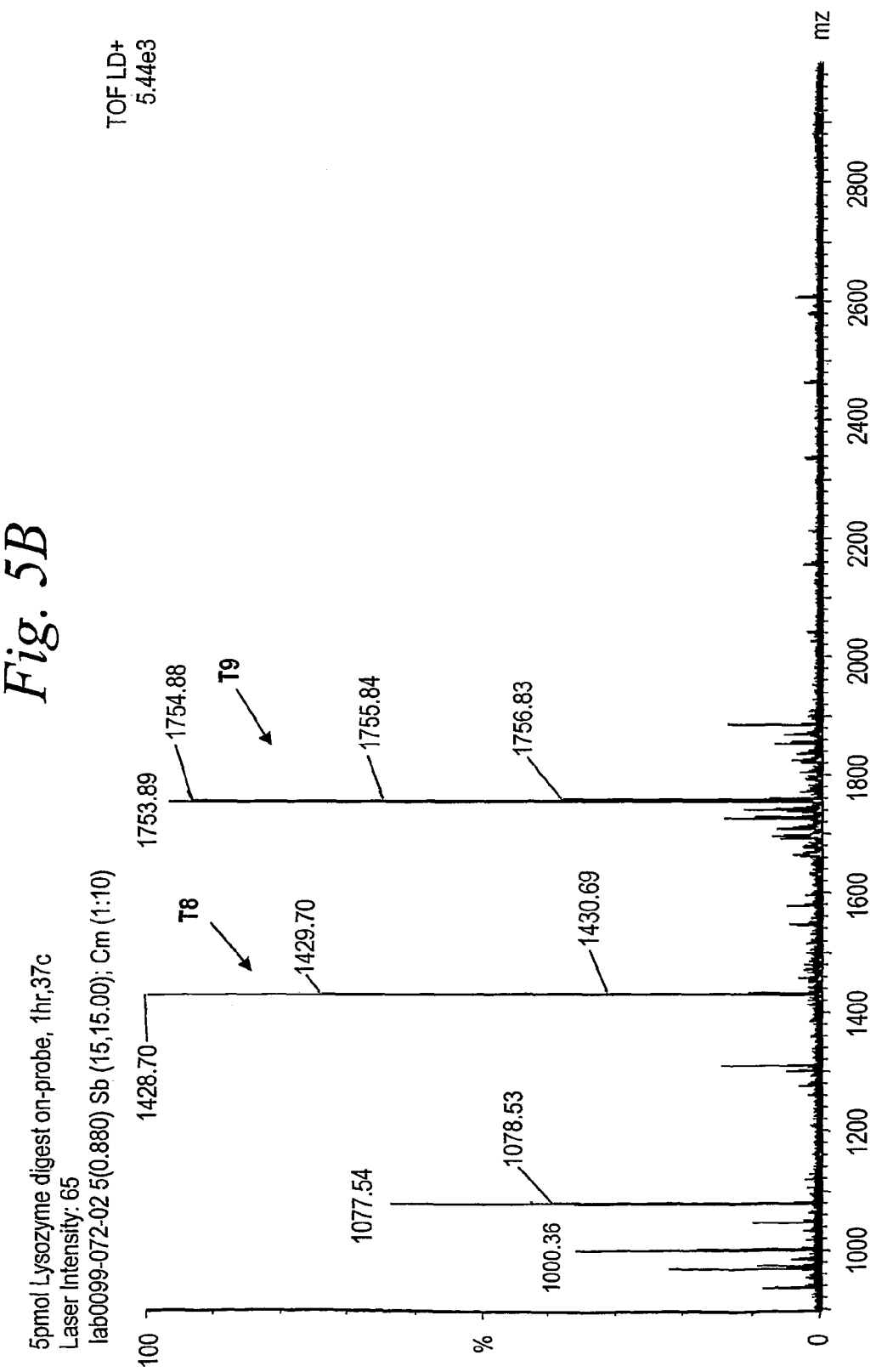

The disulfide bond of lysozyme C was reduced in the presence and absence of 0.25% ALS. The mass spectrometry analysis of the disulfide bond reduction is shown in FIG. 5.

INCORPORATION BY REFERENCE

The entire contents of all patents, published patent applications and other references cited herein are hereby expressly incorporated herein in their entireties by reference.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method for enhancing chemical digestion of a biomolecule comprising contacting the biomolecule with (i) trypsin and (ii) a surfactant represented by formula I:

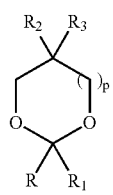

in which
p is 0, 1 or 2;
R is alkyl;
$R_1$ and $R_2$ are each, independently, hydrogen or methyl; and
$R_3$ is selected from $-OSO_3^-$, $-R_4OSO_3^-$, $-R_4OR_5SO_3^-$, and $-OR_5SO_3^-$,
wherein $R_4$ and $R_5$ are each, independently, lower alkyl; and
wherein the biomolecule is selected from the group consisting of a protein and a peptide, and
wherein the activity of said trypsin is maintained or increased upon contact with the surfactant;
thereby enhancing the chemical digestion of said biomolecule;
wherein the surfactant is degraded after the chemical digestion.

2. The method of claim 1, wherein the chemical digestion is enhanced by accelerating the rate of chemical digestion of said biomolecule, increasing the yield of chemical digestion of said biomolecule or increasing the completeness of chemical digestion of said biomolecule or a combination thereof.

3. The method of claim 1, wherein the activity of trypsin is maintained upon contact with the surfactant.

4. The method of claim 1, wherein the activity of trypsin is increased upon contact with the surfactant.

5. The method of claim 3 or 4, wherein the activity of trypsin is maintained or increased relative to the activity of trypsin in the presence of a surfactant other than the surfactant of formula I.

6. The method of claim 5, wherein the surfactant other than the surfactant of formula I is SDS.

7. The method of claim 1, further comprising the step of analyzing the biomolecule following chemical digestion thereof.

8. The method of claim 1, wherein the biomolecule is contained in a biological sample.

9. The method of claim 8, wherein the biological sample is selected from the group consisting of inclusion bodies, biological fluids, biological tissues, biological matrices, embedded tissue samples, and cell culture supernatants.

10. The method of claim 1, wherein the biomolecule is selected from the group consisting of a lipophilic protein, a receptor, a proteolytic protein, and a membrane-bound protein.

11. The method of claim 7, wherein the step of analyzing the biomolecule comprises analysis selected from the group consisting of solid phase extraction, solid phase micro extraction, electrophoresis, mass spectrometry, liquid chromatography, liquid-liquid extraction, membrane extraction, soxhlet extraction, precipitation, clarification, electrochemical detection, staining, elemental analysis, Edmund degradation, nuclear magnetic resonance, infrared analysis, flow injection analysis, capillary electrochromatography, ultraviolet detection, and combinations thereof.

12. The method of claim 11, wherein the mass spectrometry is surface desorption ionization mass spectrometry.

13. The method of claim 7, wherein the surfactant is degraded prior to analysis.

14. The method of claim 1, wherein the trypsin is immobilized.

15. The method of claim 1, wherein the biomolecule is selected from bovine serum albumin, lysozyme, ovalbumine, myoglobin, ubiquitin, and bacteriorhodopsin.

16. The method of claim 1, wherein the surfactant is degraded by contact with an acidic solution.

17. The method of claim 1, wherein the surfactant is represented by formula II:

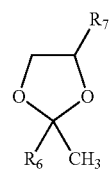

in which
$R_6$ is alkyl;
$R_7$ is selected from $-OSO_3^-$, $-R_4OSO_3^-$, $-R_4OR_5SO_3^-$, and $-OR_5SO_3^-$,
wherein $R_4$ and $R_5$ are each, independently, lower alkyl.

18. The method of claim 1 wherein the surfactant has the following chemical structure:

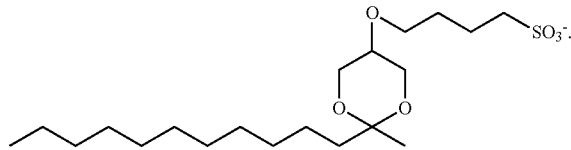

19. The method of claim 1 wherein the surfactant has the following chemical structure:

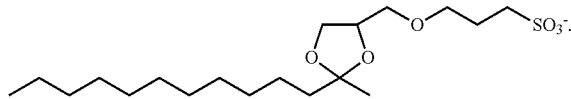

20. The method of claim 1 wherein increasing the activity of trypsin facilitates on-line automation, separation, mass spectrometric analysis, or a combination thereof.

21. The method of claim 1 wherein increasing the activity of trypsin, is performed under microscale conditions.

22. The method of claim 1 wherein the digestion occurs in an electrophoretic gel.

23. The method of claim 1 wherein the digestion occurs in the presence one or more surfactants that are different from the surfactant in Formula I.

24. The method of claim 23 wherein the digestion occurs in the presence of SDS.

25. The method of claim 1 wherein the digestion occurs in the absence of SDS.

26. A kit for increasing the activity of trypsin for the chemical digestion of a biomolecule comprising:

a surfactant represented by formula I:

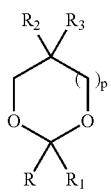

(I)

in which
p is 0, 1 or 2;
R is alkyl;
$R_1$ and $R_2$ are each, independently, hydrogen or methyl; and
$R_3$ is selected from $-OSO_3^-$, $-R_4OSO_3^-$, $-R_4OR_5SO_3^-$, and $-OR_5SO_3^-$,
wherein $R_4$ and $R_5$ are each, independently, lower alkyl; and instructions for use.

* * * * *